United States Patent
Lim et al.

(10) Patent No.: US 10,231,185 B2
(45) Date of Patent: Mar. 12, 2019

(54) METHOD FOR CONTROLLING APPARATUS ACCORDING TO REQUEST INFORMATION, AND APPARATUS SUPPORTING THE METHOD

(71) Applicant: Samsung Electronics Co., Ltd., Gyeonggi-do (KR)

(72) Inventors: Kyung Soo Lim, Gyeonggi-do (KR); Hyuk Kang, Gyeonggi-do (KR); Dong Hyun Kim, Gyeonggi-do (KR); Tae Gun Park, Gyeonggi-do (KR); Jae Bong Yoo, Gyeonggi-do (KR); Jong Ho Choi, Gyeonggi-do (KR); Jeong Min Park, Gyeonggi-do (KR); Seung Young Jeon, Gyeonggi-do (KR); Duk Ki Hong, Gyeonggi-do (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 0 days.

(21) Appl. No.: 15/120,608

(22) PCT Filed: Feb. 16, 2015

(86) PCT No.: PCT/KR2015/001549
§ 371 (c)(1),
(2) Date: Aug. 22, 2016

(87) PCT Pub. No.: WO2015/126121
PCT Pub. Date: Aug. 27, 2015

(65) Prior Publication Data
US 2017/0013562 A1  Jan. 12, 2017

(30) Foreign Application Priority Data
Feb. 22, 2014 (KR) .................. 10-2014-0020980

(51) Int. Cl.
*H04W 52/02* (2009.01)
*H04M 1/725* (2006.01)
(Continued)

(52) U.S. Cl.
CPC ........ *H04W 52/0267* (2013.01); *G04G 21/04* (2013.01); *G06F 1/163* (2013.01);
(Continued)

(58) Field of Classification Search
CPC ......... H04W 52/0267; H04W 52/0274; H04M 1/725; H04M 1/7253; Y02B 60/50
(Continued)

(56) References Cited

U.S. PATENT DOCUMENTS 8,884,874 B1 * 11/2014 Kim ..................... G06F 3/017
345/156
9,595,181 B2 * 3/2017 Katingari ............... G08B 25/10
(Continued)

FOREIGN PATENT DOCUMENTS

KR  10-2009-0041761 A  4/2009
KR  10-2009-0077606 A  7/2009
(Continued)

*Primary Examiner* — Nay A Maung
*Assistant Examiner* — Angelica M Perez
(74) *Attorney, Agent, or Firm* — Cha & Reiter, LLC

(57) ABSTRACT

A device operation method and an electronic device for supporting the same are provided. The method includes establishing a communication channel with an external device, receiving request information for requesting to activate a sensor of an electronic device in connection with executing a function of the external device, and activating the sensor in response to the request information.

16 Claims, 16 Drawing Sheets

(51) Int. Cl.
*G06F 1/16* (2006.01)
*G06F 3/0484* (2013.01)
*G04G 21/04* (2013.01)
*A61B 5/021* (2006.01)
*A61B 5/024* (2006.01)
*A61B 5/0402* (2006.01)
*A61B 5/0476* (2006.01)
*A61B 5/0488* (2006.01)
*A61B 5/1172* (2016.01)

(52) U.S. Cl.
CPC .......... *G06F 1/1626* (2013.01); *G06F 1/1698* (2013.01); *G06F 3/0484* (2013.01); *H04M 1/725* (2013.01); *H04M 1/7253* (2013.01); *H04W 52/0274* (2013.01); *A61B 5/021* (2013.01); *A61B 5/024* (2013.01); *A61B 5/0402* (2013.01); *A61B 5/0476* (2013.01); *A61B 5/0488* (2013.01); *A61B 5/1172* (2013.01); *A61B 2560/0242* (2013.01); *A61B 2562/0219* (2013.01); *A61B 2562/0247* (2013.01); *A61B 2562/0257* (2013.01); *Y02D 70/00* (2018.01); *Y02D 70/1242* (2018.01); *Y02D 70/1262* (2018.01); *Y02D 70/1264* (2018.01); *Y02D 70/142* (2018.01); *Y02D 70/144* (2018.01); *Y02D 70/162* (2018.01); *Y02D 70/164* (2018.01); *Y02D 70/166* (2018.01); *Y02D 70/168* (2018.01); *Y02D 70/26* (2018.01)

(58) Field of Classification Search
USPC .................................. 455/41.1, 41.2, 41.3
See application file for complete search history.

(56) References Cited

U.S. PATENT DOCUMENTS

| | | |
|---|---|---|
| 2003/0046401 A1 | 3/2003 | Abbott et al. |
| 2005/0240786 A1* | 10/2005 | Ranganathan ........ G06F 1/3215 713/320 |
| 2008/0140868 A1* | 6/2008 | Kalayjian ............. H04M 1/605 710/8 |
| 2010/0146356 A1* | 6/2010 | Park ...................... H03M 13/09 714/749 |
| 2011/0059769 A1 | 3/2011 | Brunolli |
| 2012/0040719 A1* | 2/2012 | Lee ........................ G06F 1/1626 455/557 |
| 2014/0354213 A1* | 12/2014 | Rivera-Poventud ........................ H02J 7/0068 320/107 |

FOREIGN PATENT DOCUMENTS

KR 10-2010-0065052 A 6/2010
KR 10-2013-0043910 A 5/2013

* cited by examiner

| SENSOR | EXTERNAL DEVICE | ELECTRONIC DEVICE |
|---|---|---|
| GPS | ON | OFF |
| ACC | OFF | OFF |
| GYRO | OFF | OFF |
| ⋮ | ⋮ | ⋮ |
|  |  |  |

FIG. 3

METHOD FOR CONTROLLING APPARATUS ACCORDING TO REQUEST INFORMATION, AND APPARATUS SUPPORTING THE METHOD

This application is a National Phase Entry of PCT International Application No. PCT/KR2015/001549, which was filed on Feb. 16, 2015, and claims a priority to Korean Patent Application No. 10-2014-0020980, which was filed on Feb. 22, 2014, the contents of which are incorporated herein by reference.

TECHNICAL FIELD

The present disclosure relates to device function control based on request information.

BACKGROUND ART

Recently, with the development of digital technologies, electronic devices, such as mobile communication devices, personal digital assistants (PDAs), electronic notes, smartphones, and tablet personal computers (PCs), which may process communication and personal information while being carried, have been released to the market in various ways. Such electronic devices reach a mobile convergence stage encompassing areas of other electronic devices without staying in their own traditional area.

Meanwhile, a conventional electronic device receives a user input through an input module such as a key button. The conventional electronic device activates a function corresponding to the received user input. Therefore, if there is no proper user input, the conventional electronic device consumes power to support functions which are not used. Also, since the conventional electronic device manually waits for a function its user needs before receiving a user input, it is impossible to provide a user function suitable for user's conditions.

DISCLOSURE

Technical Problem

Aspects of the present disclosure are to address at least the above-mentioned problems and/or disadvantages and to provide at least the advantages described below. Accordingly, an aspect of the present disclosure is to provide a device control method based on request information for recommending a function suitable for user conditions using a companion device which interworks with an electronic device and the electronic device for supporting the same.

Accordingly, another aspect of the present disclosure is to provide a device control method based on request information for using a more accurate and smooth service by performing a function, selected in a companion device by a user, in an electronic device having relative many resources and the electronic device for supporting the same.

Accordingly, another aspect of the present disclosure is to provide a device control method based on request information for minimizing operations of unnecessary device elements based on conditions between an electronic device and a companion device and the electronic device for supporting the same.

Technical Solution

In accordance with an aspect of the present disclosure, an electronic device is provided. The electronic device may include a communication interface configured to establish a communication channel with an external device and a processor (or a control module) configured to activate a sensor of the electronic device in response to request information if the request information for requesting to activate the sensor in connection to executing the external device is received through the communication interface.

In accordance with another aspect of the present disclosure, a device operation method based on request information is provided. The method may include establishing a communication channel with an external device, receiving request information for requesting to activate a sensor of an electronic device in connection with executing a function of the external device, and activating the sensor in response to the request information.

In accordance with another aspect of the present disclosure, a device operation method based on request information is provided. The method may include receiving request information from an external device communicably connected to the electronic device, activating a sensor of the electronic device based on the received request information, sending data generated based on the activated sensor to the external device, and deactivating the activated sensor, if communication with the external device is disconnected and if a battery of the electronic device is low.

Other aspects, advantages, and salient features of the disclosure will become apparent to those skilled in the art from the following detailed description, which, taken in conjunction with the annexed drawings, discloses various embodiments of the present disclosure.

Advantageous Effects

As described above, according to a device control method based on the request information and an electronic device for supporting the same according to various embodiments, the electronic device may allow its user to relatively and easily verify information associated with recommending a function by recommending the function corresponding to a user environment based on processing context information and providing the information associated with recommending the function through a companion device.

Also, according to various embodiments, the electronic device which has relative many resources may more accurately and smoothly perform a function by performing the selected function.

Also, according to various embodiments, an electronic device may efficiently operate a function and perform power control by controlling activation or deactivation of device elements in response to conditions between the electronic device and the companion device.

DESCRIPTION OF DRAWINGS

The above and other aspects, features, and advantages of certain embodiments of the present disclosure will be more apparent from the following description taken in conjunction with the accompanying drawings, in which:

FIG. 3 is a drawing illustrating a device state table according to an embodiment;

BEST MODE

Mode for Invention

Figure 1:
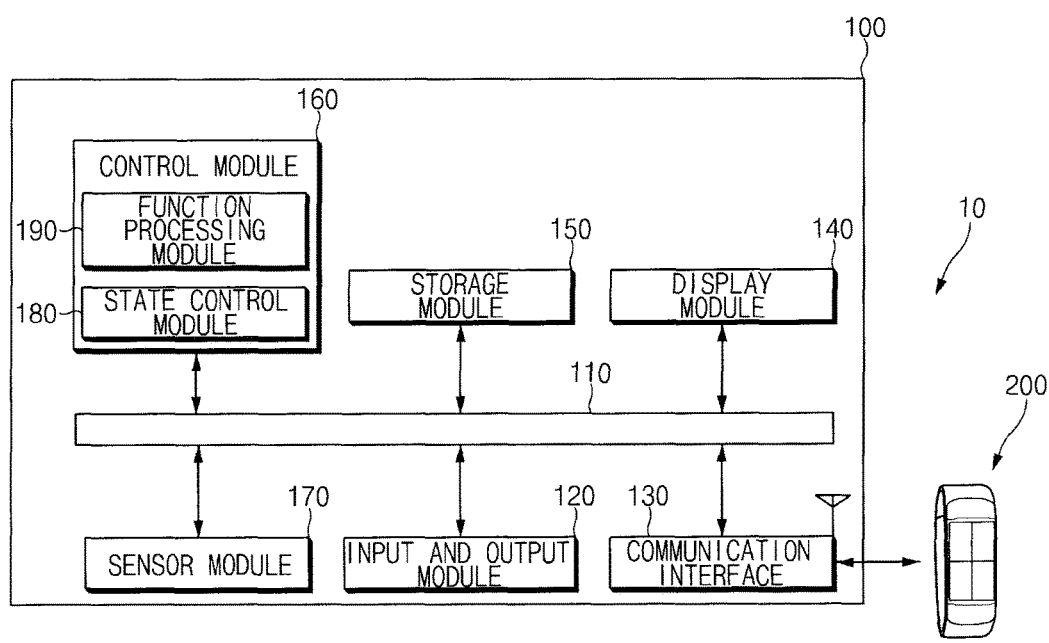
FIG. 1 is a block diagram illustrating a context information operation system according to an embodiment.

Hereinafter, the present disclosure is described with reference to the accompanying drawings. Various modifications are possible in various embodiments of the present disclosure and embodiments are illustrated in drawings and related detailed descriptions are listed. However, the present disclosure is not intended to be limited to the specific embodiments, and it is understood that it should include all modifications and/or, equivalents and substitutes within the scope and technical range of the present disclosure. With respect to the descriptions of the drawings, like reference numerals refer to like elements.

FIG. 1 is a block diagram illustrating a context information operation system according to an embodiment.

Referring to FIG. 1, a device operation system 10 according to an embodiment may include an electronic device 100 and at least one companion device or external device 200. The electronic device 100 and the external device 200 may establish a communication channel in a direct communication mode. For example, the electronic device 100 may establish a direct communication channel of a Bluetooth (BT) mode with the external device 200. Alternatively, the electronic device 100 may establish a communication channel of a wireless-fidelity (Wi-Fi) direct mode with the external device 200. This device operation system 10 may extract state related information based on at least one request information, for example, context information, collected by the electronic device 100. The electronic device 100 may generate control information based on the extracted state related information and may send the generated control information to the external device 200.

According to an embodiment, the control information may include state control information for controlling activation or deactivation of at least one of device elements of the external device 200. According to an embodiment, the control information may include user interface (UI) control information for changing a UI of the external device 200 or for outputting a specified UI. According to various embodiments, the external device 200 may receive a selection event for a specific item on the output UI. The external device 200 may send selection information corresponding to the selection event to the electronic device 100. The electronic device 100 may activate at least one device element (e.g., at least one sensor included in a sensor module 170 of the electronic device 100, a communication interface 130 (or a communication circuitry), a global positioning system (GPS) module (not shown), and the like) in connection with performing a function corresponding to the received selection information. Alternatively, the electronic device 100 may activate at least one application (e.g., a sound source play application, a video play application, a broadcast receive application, a health coaching application, and the like) in connection with performing the function corresponding to the received selection information.

According to various embodiments, in the device operation system 10, the external device 200 may collect request information, for example, context information. The external device 200 may send state related information, corresponding to the collected context information, and control information, corresponding to the state related information, to the electronic device 100. According to an embodiment, the electronic device 100 may activate or deactivate at least one device element in response to the received state related information or control information. According to an embodiment, the electronic device 100 may change a UI in response to information received from the external device 200.

As shown in FIG. 1, the electronic device 100 may include a bus 110, an input and output module 120, the communication interface 130, a display module 140, a storage module 150, the sensor module 170, and a control module 160.

The bus 110 may support to communicate data between respective components (e.g., the input and output module 120, the communication interface 130, the display module 140, the storage module 150, the sensor module 170, and the control module 160) of the electronic device 100. For example, the bus 110 may send an input signal, received from the input and output module 120, to the control module 160. The bus 110 may provide request information (e.g., context information), including at least one of location information received through the communication interface 130 or weather information, current time information, sunrise or sunset information, or message information received from another electronic device (not shown), the external device 200, or a server device (not shown) and the like, to the control module 160. The bus 110 may provide schedule information previously stored in the storage module 150 to the control module 160. The bus 110 may send control information, from the control module 160, to the communication interface 130.

The input and output module 120 may perform at least one of an input signal generation function or a data output function of the electronic device 100. The input and output module 120 may include a physical key button (e.g., a home key, a side key, a power key, and the like), a jog key, a keypad, and the like. The input and output module 120 may include a virtual keypad, output on the display module 140, as an input device. The input and output module 120 may generate an input signal for activating a specific device element, for example, the display module 140, the sensor module 170, the communication interface 130, and the like, included in the electronic device 100. According to an embodiment, the input and output module 120 may generate an input signal associated with powering on or off the electronic device 100, an input signal associated with interworking with the external device 200, and an input signal associated with state control based on context information.

According to various embodiments, the input and output module 120 may include an audio module (not shown) or a multimedia module (not shown), associated with audio processing. In this regard, the input and output module 120 may include at least one of a speaker (not shown) and a microphone (not shown). The input and output module 120 may output, for example, audio data corresponding to a communication channel when the communication channel is established with the external device 200, audio data based on collecting context information, and audio data based on sending control information. Also, the input and output module 120 may output audio data based on receiving control information from the external device 200, audio data associated with activating or deactivating a specific device element, for example, at least one sensor included in the sensor module 170, and the like. The function of outputting the audio data of the input and output module 120 may be omitted based on a user setting and the like.

The communication interface 130 may support a communication function of the electronic device 100. If the electronic device 100 supports a plurality of communication modes, it may include a plurality of communication modules. For example, the electronic device 100 may include a local-area communication module or a direct communication module in connection with establishing a direct communication channel. The local-area communication module or the direct communication module may include at least one of various communication modules such as a Wi-Fi direct communication module, a Bluetooth (BT) communication module, and a Zigbee communication module. If the electronic device 100 supports a communication mode based on a base station, the communication interface 130 may include a communication module using a 3 generation (3G)/4G (long term evolution (LTE)) network, a Wi-Fi communication module for supporting a communication mode based on an access point (AP), and the like. The communication interface 130 may include a location information collection module, for example, a GPS module.

The above-mentioned communication interface 130 may receive request information (e.g., context information) from the other electronic device, the server device, or the external device 200. The context information may include a variety of information other than the above-mentioned information. For example, the context information may include at least one of location information of the electronic device 100, weather information, time information such as sunrise/sunset information, season information, event information, official anniversary information, personal anniversary information, personal schedule information, or advertisement information. Also, the context information may include a variety of information such as information about the remaining capacity of a battery of at least one of the electronic device 100 or the external device 200 and information about a communication channel state with the external device 200. According to an embodiment, the communication interface 130 may collect current location information using the GPS module and may provide the collected current location information to the control module 160. According to an embodiment, the communication interface 130 may establish a communication channel based on a BS or a communication channel based on an AP with the server device. The communication interface 130 may receive weather information, event information, anniversary information, and the like from the server device and may provide the received information to the control module 160. According to various embodiments, a specific module, for example, the GPS module, included in the communication interface 130 may be activated or deactivated in response to selecting a function of the external device 200.

The display module 140 may output various screens associated with operating the electronic device 100. For example, the display module 140 may output a lock screen, a waiting screen, and the like. The display module 140 may output a screen of performing a specific function, for example, a screen of executing a sound source play application, a screen of executing a video play application, a screen of receiving a broadcast, and the like in response to the performance of the function. According to an embodiment, the display module 140 may output information corresponding to context information when the context information is collected through a popup window and the like. For example, the display module 140 may output schedule information, set at a current time, as context information. The display module 140 may output notification that at least one of weather information received from the server device, location information of the electronic device 100, time information, season information, event information, official anniversary information, personal anniversary information, or advertisement information is received.

According to an embodiment, the display module 140 may output information corresponding to a state where a control function of the electronic device 100 or the external device 200 is executed or is not executed based on request information, for example, context information. The display module 140 may output information corresponding to a state where the external device 200 connects to the electronic device 100. The display module 140 may output a screen associated with sending control information corresponding to received context information. The display module 140 may output a screen about receiving selection information provided from the external device 200, a screen about executing a function corresponding to selection information, and the like.

According to an embodiment, the display module 140 may output at least one of information about a communication channel state with the external device (e.g., received signal strength indication (RSSI) information, a communication channel disconnection state, a communication channel connection state, and the like), information about the remaining capacity of the battery of the electronic device 100, or information about the remaining capacity of the battery of the external device 200. The display module 140 may display an active state or an inactive state of a specific device element (e.g., the GPS module or the sensor module 170) in response to at least one of the communication channel state information or the battery remaining capacity information.

The storage module 150 (or a memory) may store a variety of information associated with operating the electronic device 100. For example, the storage module 150 may store a specific application executed in the electronic device 100, data based on executing the application, and the like. According to an embodiment, the storage module 150 may store a table associated with a device control function based on request information. The storage module 150 may provide the table to the control module 160 to support to generate control information and to control function processing.

The sensor module 170 may collect various sensor signals associated with a motion state of the electronic device 100 or a situation around the electronic device 100, and the like. For example, the sensor module 170 may include a gyro sensor, an acceleration sensor, an illumination sensor, and the like, associated with detecting motion of the electronic device 100. The sensor module 170 may be activated or deactivated by control of the electronic device 100. According to an embodiment, at least one sensor included in the sensor module 170 may be activated or deactivated under control of the control module 160 in response to selection information or request information received from the external device 200.

The control module 160 (or a processor) may process and send data associated with operating the electronic device 100 and may process and send a control signal. According to an embodiment, the control module 160 may include a state control module 180 and a function processing module 190, associated with a device control function based on request information.

Figure 2:
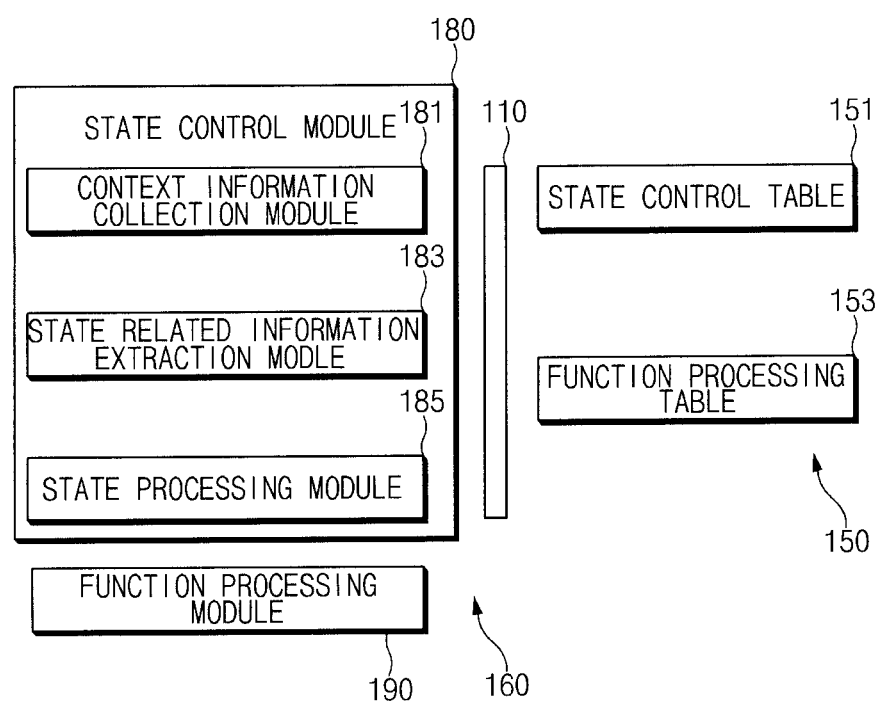
FIG. 2 is a block diagram illustrating a detailed configuration of a control module and a detailed configuration of a storage module according to an embodiment.

FIG. 2 is a block diagram illustrating a detailed configuration of a control module and a detailed configuration of a storage module according to an embodiment.

Referring to FIG. 2, a storage module 150 may include a state control table 151 and a function processing table 153.

The state control table 151 may include a state control information table, a device state table, and a UI control table. The state control information table may be a table associated with state control information among control information. According to an embodiment, the state control information table may include state control information including a command or command set to be performed in response to at least one context information. For example, the state control information table may include state information having a function to be performed when a communication channel with an external device 200 of FIG. 1 is disconnected (e.g., a communication disconnection alarm, a pause of a function which interworks with the external device 200, or a stop of executing the function, and the like) and power control information of a device element (e.g., interruption of the power supply to a communication module, interruption of the power supply to a GPS module, and the like).

According to an embodiment, the state control information table may include state control information to be executed in an electronic device 100 of FIG. 1 and state control information to be sent to the external device 200. For example, the state control information table may include state control information having a function to be performed based on a state of the remaining capacity of a battery of the electronic device 100 (e.g., a battery remaining capacity alarm, a charging request alarm, a stop of executing a function which interworks with the external device 200 when the battery of the electronic device 100 is not charged, and the like) and power control information of a device element (e.g., interruption of the power supply to the GPS module, interruption of the power supply to a sensor module 170 of FIG. 1 associated with supporting a function which interworks with the external device 200, and the like). Also, the state control information table may include state control information having a function to be performed based on a state of the remaining capacity of a battery of the external device 200 (e.g., an alarm for the remaining capacity of the battery of the external device 200, an alarm for requesting to charging the external device 200, a transfer to a function which may be performed in the electronic device 100 among functions performed in the external device 200, and the like) and power control information of a device element (e.g., interruption of the power supply to a communication module associated with a communication connection with the external device 200, interruption of the power supply to the sensor module 170 associated with interworking with the external device 200, power control of the communication module of the external device 200, power control of a sensor module of the external device 200, and the like).

The device state table may include an operation state table of at least one device element, for example, a GPS module, the sensor module 170, and the like, included in the electronic device 100. The device state table may classify and store information about a device element executed by the external device 200 in a function interworking process with the external device 200 and information about a device element executed in a process of executing a function of the electronic device 100. Therefore, table information of the device state table may be updated based on at least one of execution or end of a function which interworks with the external device 200, a communication connection state with the external device 200, or a power on/off state of the external device 200. Also, table information of the device state table associated with a device element may be updated in response to executing or ending a specific function of the electronic device 100. According to an embodiment, the device state table may have state information associated with the GPS module. If the external device 200 requests to activate the GPS module, the device state table may store a value of the GPS module as a turn-on or activation state by the external device 200. If a specified event is generated (e.g., if a communication with the external device 200 is disconnected, if a function associated with the GPS module of the external device 200 is ended, or if the external device 200 is turned off or deactivated), a value of the GPS module may be changed to a turn-off state in the device state table. The function processing module 190 may control an on/off state of device elements in response to the device state table.

The UI control table may store UI control information to be sent to the external device 200, in response to request information (e.g., context information). According to an embodiment, the UI control table may include a variety of UI control information to be sent to the external device 200, in response to schedule information. The UI control table may include each UI control information to be sent to the external device 200, based on at least one of weather information, location information, sunrise/sunset information, season information, event information, official anniversary information, personal anniversary information, or advertisement information.

According to an embodiment, the UI control table may include basic UI control information. The basic UI control information may include at least one item (e.g., A, B, C, and D). According to various embodiments, if information associated with rain is included in weather information, the basic UI control information may be changed in the form of including some (e.g., A, B, and C) of the old items, may be changed in at least one of size, location, or color of at least one of the old items, or may be changed in the form of replaced items (A, B, C, and E), in response to the weather information. According to various embodiments, the basic UI control information may be provided for at least one context information. The basic UI control information for each context information may be provided in the form of changing at least one item based on a change in a type or properties of each context information.

The function processing table 153 may include a list of function processing to be performed in the electronic device 100 in response to at least one item included in UI control information. According to an embodiment, a walking item, a running item, a cycling item, and a climbing item may be included in UI control information in connection with a health coaching function. In this case, the function processing table 153 may include a list of function processing to be performed in the electronic device 100 for each item. For example, the function processing table 153 may include a sound source play application in a list to be executed in connection with selecting the climbing item. The function processing table 153 may include a navigation function application in a list to be executed in connection with selecting the cycling item.

A state control module 180 included in a control module 160 may include a context information collection module 181, a state related information extraction module 183, and a state processing module 185.

The context information collection module 181 may collect at least one context information. The context information collection module 181 may verify schedule information stored in the storage module 150 to determine whether there is schedule information to be notified at a current time. The context information collection module 181 may collect weather information in response to a specified period or occurrence of a specific event. According to an embodiment, the context information collection module 181 may access a server device which provides weather information, when a communication channel is established with the external device 200 and may receive the weather information from the server device. According to various embodiments, if receiving feedback on execution of a specific function (e.g., a health coaching function and the like) from the external device 200, the context information collection module 181 may control access to the server device and reception of weather information. According to various embodiments, the context information collection module 181 may establish a communication channel with the external device 200 or may collect location information if a specific function is executed in the external device 200. The context information collection module 181 may monitor a state of the remaining capacity of a battery of the electronic device 100. If the remaining capacity of the battery is less than or equal to a certain value, the context information collection module 181 may collect information, indicating that the remaining capacity of the battery is less than or equal to the certain value, as context information. The context information collection module 181 may monitor a specific communication module included in a communication interface 130 of FIG. 1 (e.g., a communication module which establishes a communication channel with the external device 200). If signal strength of the communication channel is less than or equal to a certain value as a result of the monitoring or if the communication channel is disconnected as a result of the monitoring, the context information collection module 181 may collect information, indicating that signal strength of the communication channel is less than or equal to the certain value or that the communication channel is disconnected, as context information. The context information collection module 181 may send the collected context information to the state related information extraction module 183.

The state related information extraction module 183 may extract state control information using the context information, provided from the context information collection module 181, and the state control table 151. For example, the state related information extraction module 183 may detect state control information corresponding to the received context information from the state control information table. The state related information extraction module 183 may send the extracted state control information to the state processing module 185.

The state processing module 185 may send the state control information to the external device 200. The state processing module 185 may send UI control information for each context information, corresponding to the state control information or specific context information, to the external device 200. According to various embodiments, if at least part of the state control information is information applied to the electronic device 100, the state processing module 185 may send the corresponding information to a function processing module 190.

The function processing module 190 may output an alarm corresponding to the state control information provided from the state processing module 185 and may process a function corresponding to the state control information. Also, the function processing module 190 may verify a function processing list, corresponding to selection information received from the external device 200, with reference to the function processing table 153. The function processing module 190 may control execution of a function registered in the function processing list. For example, the function processing module 190 may automatically activate a sound source play application in response to selection information received from the external device 200 and may output reproduced audio data. In this process, the function processing module 190 may delivery (or send) audio data to an accessory device (e.g., a headset, an earphone, a wireless headset, a wireless speaker, and the like) connected to the electronic device 100. The function processing module 190 may reproduce (or replay) at least one of sound sources stored in a storage module 150 of FIG. 1 or may replay a sound source based on a previously defined sound source list.

According to various embodiments, the function processing module 190 may maintain a state of a display module 140 of FIG. 1 as a previous state in a process of processing a specific function. For example, the function processing module 190 may control reproduction of a sound source and an output of the reproduced sound source while keeping the display module 140 turned off. Alternatively, the function processing module 190 may sets the display module 140 to a specific screen state (e.g., a waiting screen state or a home screen state, and a specific menu screen state), and may reproduce a sound source and may output a reproduced sound source through background processing.

FIG. 3 is a drawing illustrating a device state table according to an embodiment.

Referring to FIG. 3, the device state table may include, for example, state information for each device operation of specific device elements (e.g., a GPS module GPS, an acceleration sensor ACC, a gyro sensor GYRO) included in an electronic device 100 of FIG. 1. A GPS module item in the device state table may represent a state where the GPS module is turned on by an external device 200 of FIG. 1. The GPS module item may represent a state where the GPS module is turned off by the electronic device 100. In this regard, the GPS module of the electronic device 100 may be activated by currently having a turn-on state.

According to various embodiments, if a communication channel is disconnected between the external device 200 and the electronic device 100 or if the external device 200 is turned off, a control module 160 of FIG. 1 may switch the GPS module to a turn-off state. In this case, a value of the GPS module associated with the external device 200 in the device state table may be changed from a turn-on state to the turn-off state.

According to various embodiments, if a value of the GPS module is the turn-on state in response to executing a specific function (e.g., a navigation function) of the electronic device 100, although communication with the external device 200 is disconnected or although the external device 100 is changed to the turn-off state, the control module 160 may keep the GPS module turned on.

As described above, the device state table may store information about whether device elements included in the electronic device 100 have the turn-on state or the turn-off state in connection with performing a function of the external device 200. Also, the device state table may store information about whether the device elements included in the electronic device 100 have the turn-on state or the turn-off state in connection with performing a function of the electronic device 100. The control module 160 may restore a device element of the electronic device 100, having the turn-on state or the turn-off state by the external device 200, to an original state in response to at least one of a communication disconnection with the external device 200, the remaining capacity of a battery of the external device 200, the turn-off state of the external device 200, or end of a specific function of the external device 200. In this process, the control module 160 may verify information of a device state table associated with the electronic device 100 with respect to device elements (e.g., the GPS module, a sensor module 170 of FIG. 1, a communication interface 130 of FIG. 1 associated with accessing a server device, and the like) and may control the device elements to have a state corresponding to information stored in the device state table.

According to various embodiments, the device state table may represent operation states of specific device elements (e.g., the GPS module, the sensor module 170, and the like) of the electronic device 100 in response to a communication connection or disconnection state between the electronic device 100 and the external device 200 or a state of the remaining capacity of the battery of the electronic device 100 or the external device 200. For example, the device state table may include state information of at least one sensor included in the sensor module 170 of the electronic device 100, activated by a request of the electronic device 100 when a communication channel is not established between the electronic device 100 and the external device 200 under control of the control module 160. The device state table may include state information of the GPS module activated based on a request of the external device 200 upon a communication connection between the electronic device 100 and the external device 200 under control of the control module 160 and state information of at least one sensor included in the sensor module 170 activated in response to a request of the external device 200 and a request of the electronic device 100.

According to various embodiments, the device state table may include information about a state where an operation of the GPS module activated by the external device 200 pauses upon a communication disconnection between the electronic device 100 and the external device 200 under control of the control module 160 and information about a state where a sensor activated according to a request of the external device 200 is deactivated. Therefore, the electronic device 100 may pause for operating the GPS module, activated in connection with supporting the external device 200, during a certain time. The device state table may include state information of the GPS module deactivated at a battery low state of the electronic device 100 under control of the control module 160 and information about a state where a sensor activated according to a request of the external device 200 and the electronic device 100 is deactivated. In this state, the electronic device 100 may send a warning message for the battery low state of the electronic device 100 to the external device 200. Also, the electronic device 100 may deactivate the sensor module 170 which is requested by the external device 200 or is not used to operate a specific function of the electronic device 100. The device state table may include information about a state where the GPS module is kept activated in a battery low state of the external device 200 under control of the control module 160 and information about a state where a sensor activated based on a request of the external device 200 and a request of the electronic device 100 is kept activated. In this state, the electronic device 100 may send a warning message for the battery low state of the external device 200 to the external device 200.

In the above-mentioned description, the device elements of the device state table are exemplified as the GPS module, the acceleration sensor, and the gyro sensor. However, various embodiments are not limited thereto. For example, the device state table may further include device state information of various elements such as an illumination sensor, a microphone associated with performing a voice recognition function, a headset or ear-set associated with an audio output, and a communication module associated with an audio output.

According to various embodiments, the electronic device 100 may include a control module 160 configured to extract state related information corresponding to context information associated with an external device 200 communicably connected with the electronic device 100 and to control at least one of the external device 200 or the electronic device 100 based on the state related information and at least one device element configured to be activated or deactivated in connection with operating the external device 200 in response to control of the control module 160.

According to various embodiments, the electronic device 100 may further include at least one of a communication interface 130 configured to receive at least one of weather information, location information, time information, season information, event information of a certain area, advertisement information, information about the remaining capacity of a battery of the external device 200, or information about a communication channel state with the external device 200 and a storage module 150 configured to store at least one of official anniversary information, personal anniversary information, personal schedule information, or information about the remaining capacity of a battery of the electronic device 100.

According to various embodiments, the control module 160 may generate state control information for controlling activation or deactivation of at least one of device elements of the external device 200 and at least one of device elements of the electronic device 100 based on the state related information.

According to various embodiments, the control module 160 may activate a device element of the electronic device 100, associated with supporting a function executed in the external device 200 upon a communication connection between the electronic device 100 and the external device 200.

According to various embodiments, if communication between the electronic device 100 and the external device 200 is disconnected, the control module 160 may pause for or deactivate an operation of a device element of the electronic device 100, associated with supporting a function executed in the external device 200.

According to various embodiments, if the electronic device 100 enters a low battery state in a state where communication between the electronic device 100 and the external device 100 is connected, the control module 160 may deactivate a device element of the electronic device 100, associated with supporting a function executed in the external device 200, and at least one device element which is being executed in the electronic device 100.

According to various embodiments, if the external device 200 enters a low battery state in a state where communication between the electronic device 100 and the external device 200 is connected, the control module 160 may deactivate a device element of the electronic device 100, activated in connection with the external device 200.

According to various embodiments, the control module 160 may maintain a device element which is being operated in the electronic device 100 among device elements activated in connection with the external device 200 in an activated state.

According to various embodiments, the control module 160 may generate screen interface control information, associated with controlling a screen interface of the external device 200, based on the state related information and may send the screen interface control information to the external device 200.

According to various embodiments, the control module 160 may receive selection information corresponding to selection of at least one item included in the screen interface from the external device 200 and may activate a device element of the electronic device 100 or a specific application of the electronic device in response to the received selection information.

According to various embodiments, an electronic device may include a communication interface configured to establish a communication channel with an external device and a control module configured to activate a sensor of the electronic device in response to request information if the request information for requesting to activate the sensor in connection with executing the external device is received.

According to various embodiments, the control module may send at least part of a sensor signal collected by the activated sensor and at least one of signals processed based on the sensor signal to the external device.

According to various embodiments, the control module may deactivate the activated sensor based on at least one of an event associated with ending a function executed in the external device, an event associated with a communication disconnection with the external device, or an event associated with a change of the remaining capacity of a battery of the external device or the electronic device.

According to various embodiments, the control module may restore a state of the sensor to a state before the external device connects with the electronic device in response to the occurrence of the event.

According to various embodiments, the control module may generate screen interface control information to be outputted on the external device based on collected context information and may send the screen interface control information to the external device.

According to various embodiments, the control module may output an object for selecting at least one function executable in the external device on a sub display module of the external device based on collected context information.

According to various embodiments, if specific function selection information is received from the external device, the control module may output at least one application selection item, associated with the received function selection information, on a display module of the electronic device or may automatically activate the at least one application selection item.

According to various embodiments, the control module may collect the context information, including at least one of weather information, location information, time information, season information, event information of a certain area, advertisement information, information about the remaining capacity of a battery of the external device, or information about a communication channel state with the external device based on the communication interface or at least one of official anniversary information, personal anniversary information, personal schedule information or information about the remaining capacity of a battery of the electronic device, each of which is stored in a storage module of the electronic device.

According to various embodiments, the control module may generate and store a state information table for at least one of a sensor of the electronic device, activated or deactivated by a request of the external device, or a sensor of the electronic device, activated or deactivated by a request of the electronic device.

According to various embodiments, if the activation or deactivation of the sensor is changed by a request of the external device or a communication disconnection with the external device, the control module may update the state information table.

Figure 4:
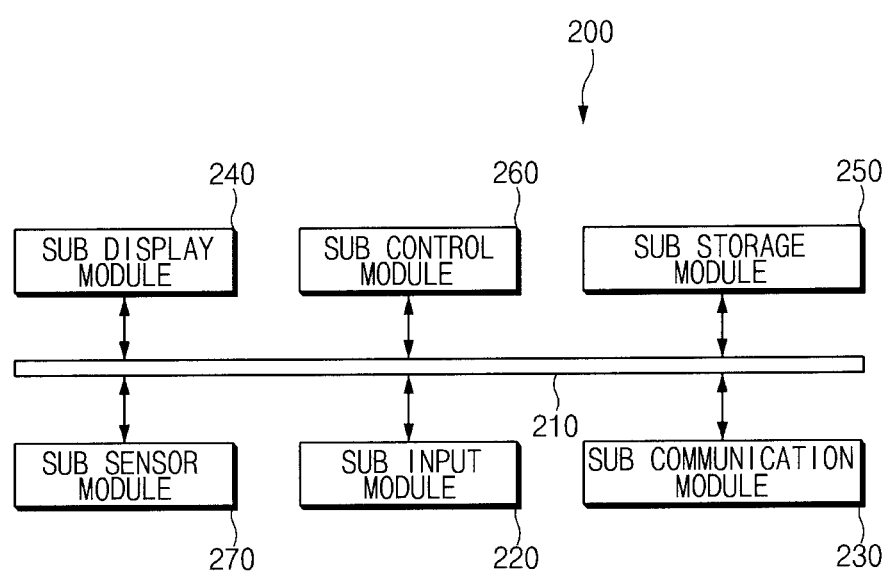
FIG. 4 is a block diagram illustrating an external device according to an embodiment.

FIG. 4 is a block diagram illustrating an external device according to an embodiment.

Referring to FIG. 4, an external device 200 may include a sub bus 210, a sub input module 220, a sub communication module 230, a sub display module 240, a sub storage module 250, a sub sensor module 270, and a sub control module 260. In addition, the external device 200 may further include an audio module for outputting or collecting audio data.

The sub bus 210 may send a signal between the sub input module 220, the sub communication module 230, the sub display module 240, the sub storage module 250, the sub sensor module 270, and the sub control module 260. According to an embodiment, the sub bus 210 may send state control information, received by the sub communication module 230, to the sub control module 260. The sub bus 210 may send UI control information, received by the sub communication module 230, to the sub display module 240 in response to control of the sub control module 260. The sub bus 210 may send an event, generated from the sub display module 240 or the sub input module 220, to the sub control module 260 and may send the generated event to the sub communication module 230 in response to control of the sub control module 260.

The sub input module 220 may generate an input signal associated with operating the external device 200. The sub input module 220 may include a physical key such as a home key. If the sub display module 240 includes a touch function, the sub display module 240 may operate as the sub input module 220. The sub input module 220 may generate, for example, an event for selecting a specific item on a UI including at least one item output on the sub display module 240. The generated event may be sent to the sub control module 260.

The sub communication module 230 may establish a communication channel with the external device 100. The sub communication module 230 may be, for example, a communication module (e.g., a BT communication module, a Wi-Fi direct communication module, and the like) for establishing a direct communication channel. The sub communication module 230 may receive at least one of state control information or UI control information from the electronic device 100. The sub communication module 230 may send selection information, for selecting a specific icon or a specific menu item on an icon screen or a menu screen of the external device 200, to the electronic device 100. The sub communication module 230 may send event information, for selecting a specific item on a UI output on the sub display module 240, to the electronic device 100. According to various embodiments, the sub communication module 230 may send context information associated with the external device 200 (e.g., information about the remaining capacity of a battery of the external device 200, information about end of a specific function of the external device 200, and the like) to the external device 100.

The sub display module 240 may output a screen associated with operating the external device 200. For example, the sub display module 240 may output a waiting screen, a menu screen, and the like of the external device 200. According to an embodiment, the sub display module 240 may output a watch information screen, a health coaching application icon output screen, a schedule information screen, and the like. According to an embodiment, the sub display module 240 may output a screen corresponding to basic UI control information received from the electronic device 100. Also, the sub display module 240 may output a screen corresponding to change UI control information changed by context information collected by the electronic device 100. The sub display module 240 may output a screen based on selection of at least one item included in a screen corresponding to UI control information, an information output screen associated with executing a corresponding item, and the like.

The sub storage module 250 may store an application and data necessary for operating the external device 200. For example, the sub storage module 250 may store content associated with a screen corresponding to UI control information received from the electronic device 100. Herein, the content may include at least one item image and text information. The sub storage module 250 may store UI control information provided from the electronic device 100.

The sub sensor module 270 may include at least one sensor operated in the external device 200. For example, the sub sensor module 270 may include a gyro sensor. The sub sensor module 270 may include an image sensor. If the external device 200 performs a specific function by interworking with the electronic device 100, a sensor duplicated with a sensor module 170 of FIG. 1 which is being operated in the electronic device 100 may be deactivated. A sensor which is in an activated state and is then deactivated by an operation of a sensor of the electronic device, included in the sub sensor module 270, may be automatically activated, if a communication channel with the electronic device 100 is disconnected or if the electronic device 100 is turned off.

The sub control module 260 may process and send data of the external device 200 and may process and send a control signal. According to an embodiment, the sub control module 260 may control the sub communication module 270 to establish a communication channel with the electronic device 100 in response to an event generated by the sub input module 220 or a communication connection request of the electronic device 100. If at least one of state control information or UI control information is received from the electronic device 100, the sub control module 260 may process the received information. For example, the sub control module 260 may control activation or deactivation of at least one sensor included in the sub sensor module 270 in response to state control information. The sub control module 260 may control an alarm of the remaining capacity of a battery of at least one of the electronic device 100 or the external device 200, an alarm for requesting to charging the external device 200, a transfer to a function which may be performed in the electronic device 100 among functions performed in the external device 200, and the like, in response to state control information. According to various embodiments, the sub control module 260 may output a screen, including at least one item, on the sub display module 240 in response to received UI control information. If a specific item is selected, the sub control module 260 may send the selected information to the electronic device 100.

Figure 5:
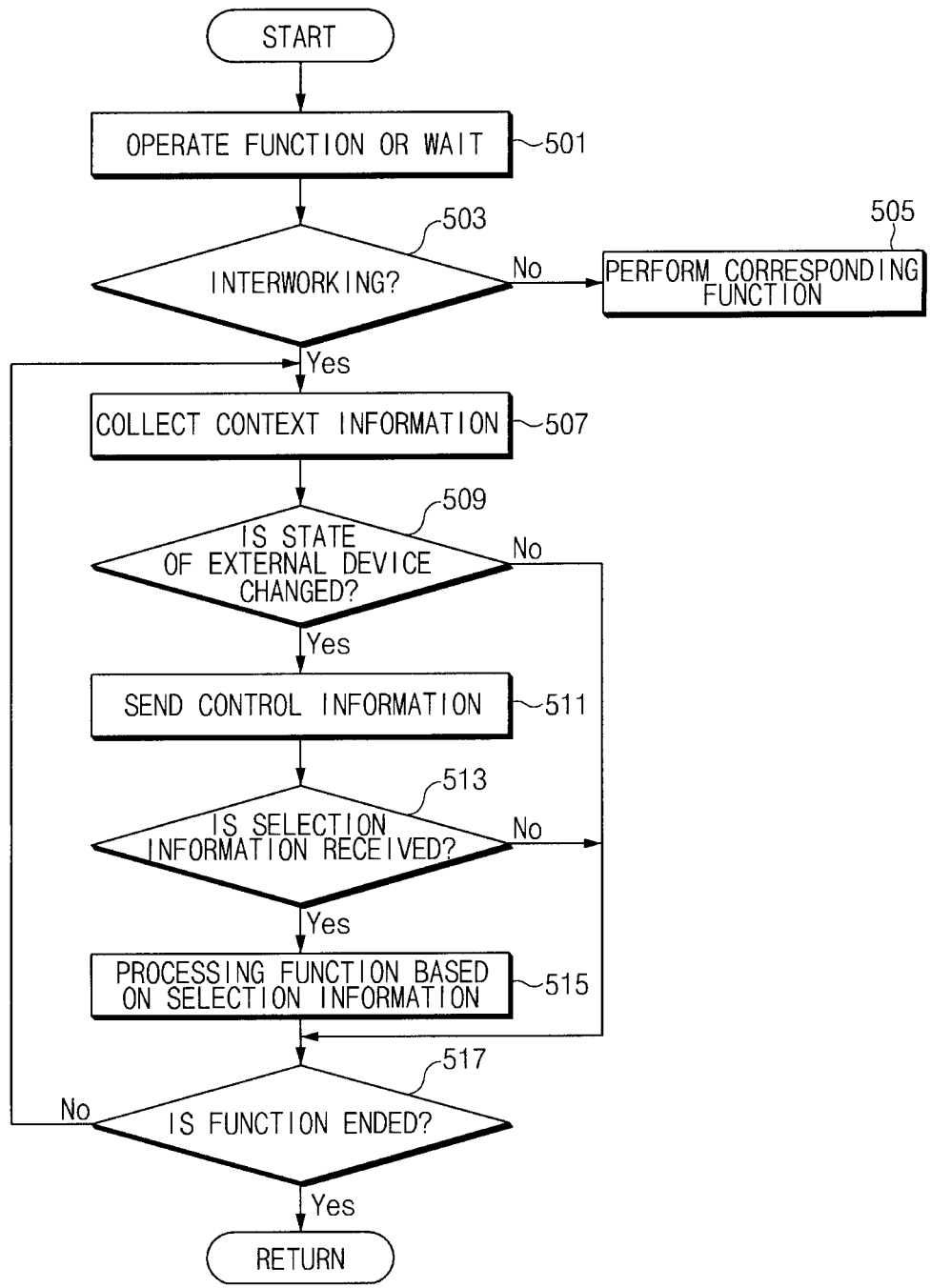
FIG. 5 is a flowchart illustrating an electronic device operation method according to an embodiment.

FIG. 5 is a flowchart illustrating an electronic device operation method according to an embodiment.

Referring to FIG. 5, in operation 501, a control module 160 of FIG. 1 may operate a function or may wait. For example, the control module 160 may output a waiting screen or a specific menu screen. Alternatively, the control module 160 may output a screen based on performing a specific function, may have a sleep state, or may output a lock screen. According to an embodiment, the control module 160 may output a screen including a specific function icon or a specific menu for instructing to interwork with an external device 200 of FIG. 1. Alternatively, the control module 160 may control a communication interface 130 of FIG. 1 to have a communication waiting state which may response to a scan operation of the external device 200.

In operation 503, the control module 160 may determine whether an event associated with an interworking function is generated. According to an embodiment, the control module 160 may determine whether an event based on selection of an icon or menu for instructing to interwork with the external device 200 is generated. According to an embodiment, the control module 160 may determine whether a schedule event associated with interworking with the external device 200 is generated. According to an embodiment, the control module 160 may determine whether an event corresponding to receiving a communication connection request message from the external device 200 is generated. Alternatively, the control module 160 may determine whether an application activation request event necessary for interworking with the external device 200 is generated. If the event associated with the interworking function is not generated, in operation 505, the control module 160 may perform a corresponding function. For example, the control module 160 may execute a specific function (e.g., a sound source pay function, a broadcast receive function, a telephony function, and the like) corresponding to a type of the generated event or may apply a corresponding event function to a previously executed function. Alternatively, the control module 160 may change the electronic device 100 to a sleep mode or a tune-off state based on a type of the event.

If the event associated with the interworking function is generated in operation 503, the control module 160 may establish a communication channel with the external device 200. For example, the control module 160 may control the communication interface 130 to establish a communication channel of a BT communication mode or a Wi-Fi direct communication mode with the external device 200. In operation 507, the control module 160 may collect context information. According to various embodiments, the control module 160 may collect context information. If specified context information is collected, the control module 160 may establish a communication channel with the external device 200.

The control module 160 may verify the collected context information. In operation 509, the control module 160 may determine whether there is context information associated with a state change of the external device 200. If there is the context information associated with the state change of the external device 200, the control module 160 may generate control information corresponding to the context information. As described above, the control information may include at least one of state control information for controlling activation or deactivation of at least one of device elements of the external device 200 or UI control information associated with controlling a UI of the external device 200. In operation 511, the control module 160 may send the control information to the external device 200.

In operation 513, the control module 160 may determine whether selection information is received from the external device 200. Herein, the selection information may be information corresponding to selection of at least one of at least item included in a UI of the external device 200.

If the selection information is received in operation 513, in operation 515, the control module 160 may process a function based on the selection information. For example, if selection information corresponding to selection of an item associated with performing a specific function is received from the external device 200, the control module 160 may activate a device element of the electronic device 100, associated with performing the corresponding function or may activate an application associated with performing the corresponding function.

In operation 517, the control module 160 may determine whether an event associated with ending the function is generated. If the event associated with ending the function is not generated in operation 517, the control module 160 may branch to operation 507 and may perform the operations again from operation 507. According to various embodiments, if the event associated with ending the function is not generated in operation 517, the control module 160 may branch to operation 515 to maintain to process a function based on selection information. If the event associated with ending the function is generated in operation 517, the control module 160 may end the interworking function with the external device 200 and may branch to operation 501 to perform the operations again from operation 501. In this operation, the control module 160 may deactivate the communication interface 130, a GPS module, and the sensor module 170 including at least one sensor, activated in connection with supporting the interworking function with the external device 200.

If the context information associated with the state change of the external device 200 is not collected in operation 509, the control module 160 may skip operations 511 to 515 to branch to operation 517. Also, if the selection information is not received within a certain time from the external device 200 in operation 513, the control module 160 may skip operation 515 to branch to operation 517.

Figure 6:
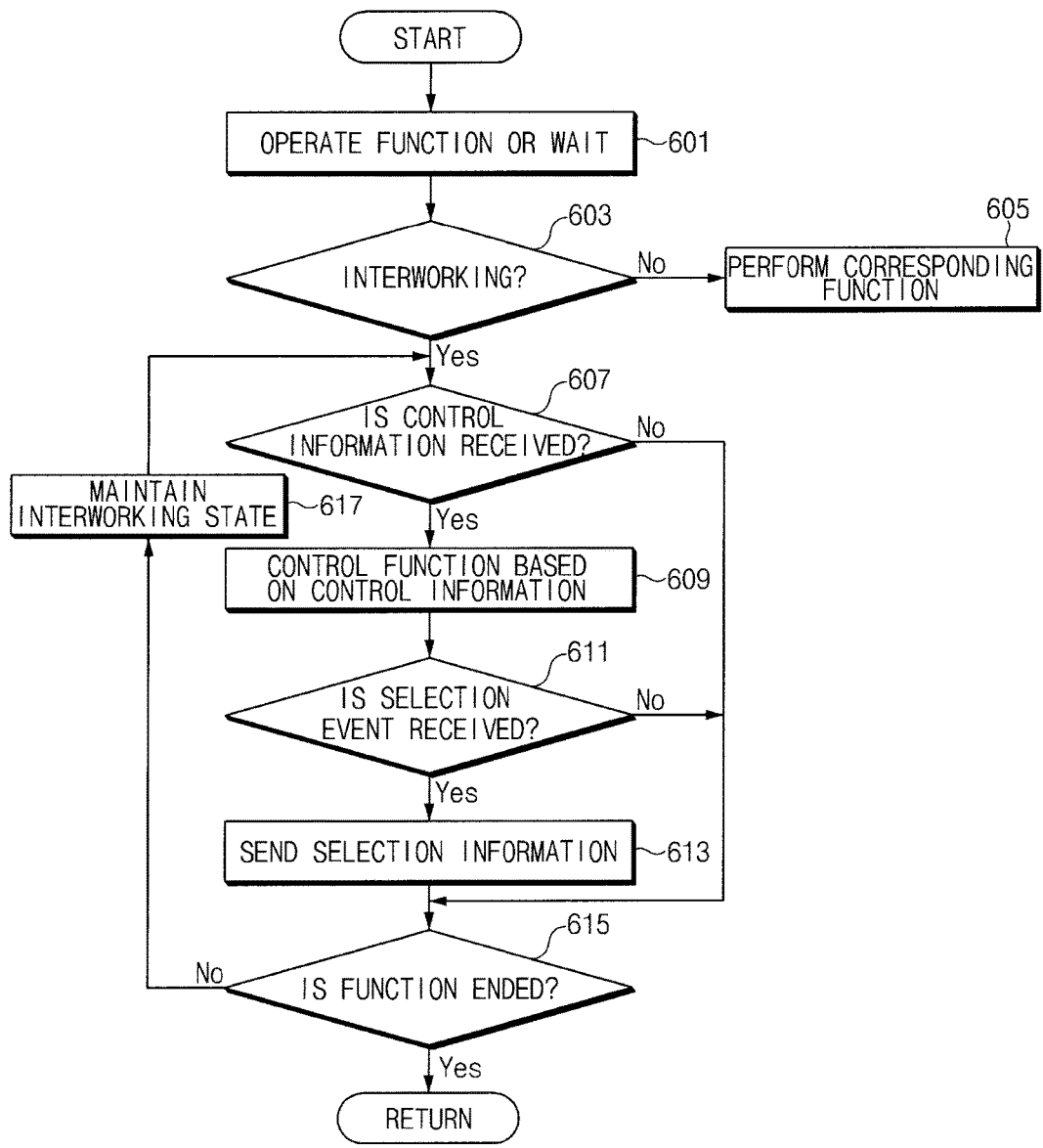
FIG. 6 is a flowchart illustrating an external device operation method according to an embodiment.

FIG. 6 is a flowchart illustrating an external device operation method according to an embodiment.

Referring to FIG. 6, in operation 601, a sub control module 260 of an external device 200 of FIG. 4 may operate a function or may wait. For example, the external device 200 may perform a watch function, a schedule information output function, or a communication waiting function in operation 601. Alternatively, the external device 200 may output a function icon or menu associated with an interworking function with an electronic device 100 of FIG. 1. Alternatively, the external device 200 may assign a specific key button associated with an interworking function with the electronic device 100. Alternatively, the external device 200 may have a communication waiting state for corresponding to a scan operation from the electronic device 100.

In operation 603, the sub control module 260 may determine whether an event associated with the interworking function is generated. For example, the sub control module 260 may determine whether an event corresponding to selection of the function icon or menu associated with executing the interworking function or selection of the key button associated with executing the interworking function is generated. Alternatively, the sub control module 260 may determine whether an event corresponding to receiving a communication connection request message from the electronic device 100 is generated. According to various embodiments, the sub control module 260 may determine whether an activation request message of a specific application (e.g., a health coaching application, a disease management function application, and the like) requested to interwork with the electronic device 100 is generated.

If the event associated with interworking function is not generated, in operation 605, the sub control module 260 may perform a specific function. For example, the sub control module 260 may perform a specific function (e.g., a watch display function, a weather display function, a pedometer function, a photoplethysmography (PPG) detection function, and the like) of the external device 200. Alternatively, the sub control module 260 may change the external device 200 to a sleep mode state (e.g., a turn-off state of a sub display module 240 of FIG. 4, a low-power operation mode, and the like). Alternatively, if an event associated with turning off the external device 200 is generated, the sub control module 260 may change the external device 200 to a turn-off state.

If the event associated with the interworking function is generated, the sub control module 260 may establish a communication channel with the external device 100. In operation 607, the sub control module 260 may determine whether control information is received. If the control information is received, in operation 609, the sub control module 260 may control a function based on the control information.

According to an embodiment, if state control information is received from the electronic device 100, the sub control module 260 may control activation or deactivation of at least one sensor included in a sub sensor module 270 of FIG. 4 in response to the state control information. According to an embodiment, the sub control module 260 may change a sub communication module 230 of FIG. 4 to a deactivated state in response to the state control information. According to various embodiments, the sub control module 260 may output a warning message (e.g., an alarm message indicating that a communication state with the electronic device 100 is a weak electric field state, an alarm message for a low battery state of the electronic device 100, an alarm message for a low battery state of the electronic device 200, and the like) sent from the electronic device 100 upon receiving the state control information.

According to an embodiment, the sub control module 260 may receive UI control information from the electronic device 100. The sub control module 260 may output a UI corresponding to the UI control information to the sub display module 240. Herein, the UI control information may include UI related information (e.g., a background screen information, item image and text information, location information of an item, and the like) to be output on the sub display module 240 of the external device 200. Alternatively, the UI control information may include instruction information for instructing to output at least one specific item of UI related information stored in a sub storage module 250 of the external device 200 to a specific location in a specific form.

If the UI control information is received in operation 609, in operation 611, the sub control module 260 may determine whether a selection event for selecting a specific item (e.g., a specific function icon or a specific menu item) included in a screen of the sub display module 240 is received. If the selection event is received in operation 611, in operation 613, the sub control module 260 may send selection information corresponding to the selection event to the electronic device 100. According to various embodiments, if the state control information is received, the sub control module 260 may skip operations 611 and 613 after operation 609 to branch to operation 615. If the control information is not received in operation 607, the sub control module 260 may skip operations 609 to 613 to branch to operation 615. Also, if the selection event is not generated within a certain time in operation 611, the sub control module 260 may skip operation 613 to branch to operation 615.

In operation 615, the sub control module 260 may determine whether an event associated with ending the function is generated. If the event associated with ending the function is not generated, the sub control module 260 may branch to operation 617 to maintain an interworking state with the external device 200. The sub control module 260 may perform the operations again from operation 607. If the event associated with ending the function is generated, the sub control module 260 may branch to operation 601 to perform the operations again from operation 601.

Figure 7:
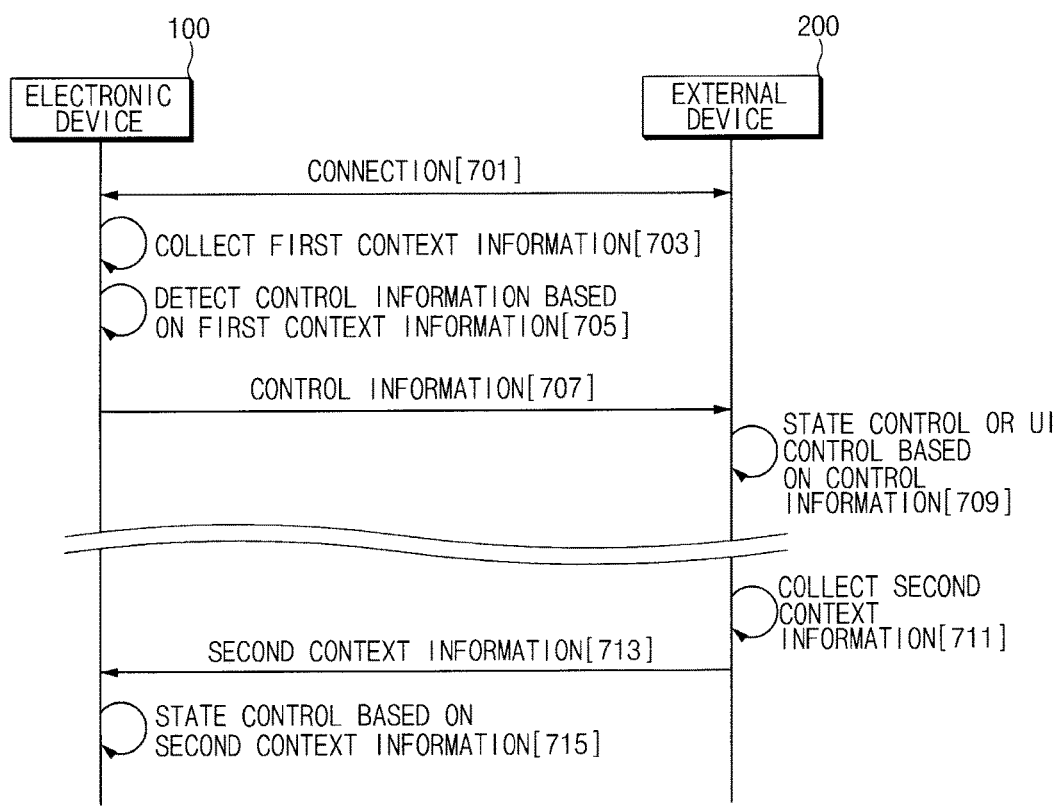
FIG. 7 is a signal sequence diagram illustrating a context information operation system according to an embodiment.

FIG. 7 is a signal sequence diagram illustrating a context information operation system according to an embodiment.

Referring to FIG. 7, in operation 701, an electronic device 100 and an external device 200 may have a connection state. In this regard, the electronic device 100 may scan the external device 200 based on a default setting upon receiving power to attempt to establish a communication channel with the external device 200. Alternatively, the electronic device 100 may attempt to establish a communication channel with the external device 200 at a certain period, upon activating a specific application, or upon requesting to interwork with external device 200. According to various embodiments, the external device 200 may scan the electronic device 100 based on a default setting upon receiving power to attempt to establish a communication channel with the electronic device 100. Alternatively, as described above, if an event for requesting to activate a specific application or to interwork with the electronic device 100 is generated, the external device 200 may attempt to establish a communication channel with the electronic device 100.

In operation 703, the electronic device 100 may collect first context information. Herein, the first context information may include message information, advertisement information, schedule information, location information, weather information, time information, season information, event information, information associated with a communication connection state with the external device 200, information associated with a communication connection between the electronic device 100 and another electronic device, and the like, each of which is collected through a communication interface 130 of the electronic device 100. Also, the first context information may include schedule information, information associated with a battery state of the electronic device 100, and the like, each of which is stored in a storage module 150 of the electronic device 100. In operation 705, the electronic device 100 may detect control information based on the first context information. In operation 707, the electronic device 100 may send the detected control information to the external device 200.

If receiving the control information from the electronic device 100, in operation 709, the external device 200 may perform state control or UI control based on the control information. For example, the external device 200 may control activation or deactivation of at least one of a sub sensor module 270 and a sub communication module 230 of FIG. 4. The external device 200 may output a specific UI based on the UI control on a sub display module 240 of FIG. 4.

According to various embodiments, in operation 711, the external device 200 may collect second context information. The external device 200 may collect information associated with a battery state of the external device 200, information associated with a communication connection state with the electronic device 100, specific function execution information, information associated with a time which elapses after a specific function is executed, and the like as the second context information. In operation 713, the external device 200 may send the collected second context information to the electronic device 100.

If receiving the second context information from the external device 200, in operation 715, the electronic device 100 may perform state control corresponding to the second context information. For example, the electronic device 100 may activate or deactivate at least one sensor included in a sensor module 170 of the electronic device 100 in response to the second context information. The electronic device 100 may control activation or deactivation of a communication interface 130 (e.g., a GPS module, a communication module which supports a direct communication mode, and the like) of the electronic device 100 or may control a pause in operation of the communication interface 130, in response to the second context information. The electronic device 100 may send a specified warning message or a specified alarm message to the external device 200 in response to the second context information.

According to various embodiments, a device operation method may include collecting context information, extracting state related information associated with controlling an external device 200 communicably connected to an electronic device 100 from the context information, and controlling at least one of the external device 200 or the electronic device 100 based on the state related information.

According to various embodiments, the collecting of the context information may include at least one of collecting at least one of weather information, location information, time information, season information, event information of a certain area, advertisement information, information associated with the remaining capacity of a battery of the external device 200, or information associated with a communication channel state with the external device 200 using a communication interface 130 or collecting at least one of official anniversary information, personal anniversary information, personal schedule information, or information associated with the remaining capacity of a battery of the electronic device 100 based on information stored in a storage module 150.

According to various embodiments, the controlling of the at least one may include generating state control information for controlling activation or deactivation of at least one of device elements of the external device 200 and at least one of device elements of the electronic device 100 based on the state related information.

According to various embodiments, the controlling of the at least one may further include activating a device element of the electronic device 100, associated with supporting a function executed in the external device 200 upon a communication connection between the electronic device 100 and the external device 200.

According to various embodiments, the controlling of the at least one may further include pausing for or deactivating an operation of a device element of the electronic device 100, associated with supporting a function executed in the external device 200, if communication between the electronic device 100 and the external device 200 is disconnected.

According to various embodiments, the controlling of the at least one may further include deactivating a device element of the electronic device 100, associated with supporting a function executed in the external device 200, and at least one device element which is being executed in the electronic device 100, if the electronic device 100 enters a low battery state in a state where the electronic device 100 and the external device 100 are communicably connected with each other, According to various embodiments, the controlling of the at least one may include deactivating a device element of the electronic device 100, activated in connection with the external device 200, if the external device 200 enters a low battery state in a state where the electronic device 100 and the external device 200 are communicably connected with each other, According to various embodiments, the method may further include maintaining a device element, which is being operated in the electronic device 100, among device elements activated in connection with the external device 200, in an activated state.

According to various embodiments, the controlling of the at least one may include generating screen interface control information associated with controlling a screen interface of the external device 200 based on the state related information and sending the screen interface control information to the external device 200.

According to various embodiments, the controlling of the at least one may include receiving selection information corresponding to selection of at least one item included in the screen interface from the external device 200 and activating a device element of the electronic device 100 or a specific application of the electronic device in response to the received selection information.

According to various embodiments, a device operation method based on request information may include establishing a communication channel with an external device, receiving request information for requesting to activate a sensor of an electronic device in connection with executing a function of the external device, and activating the sensor in response to the request information.

According to various embodiments, the method may further include sending at least part of a sensor signal collected by the activated sensor and at least one of signals processed based on the sensor signal to the external device.

According to various embodiments, the method may further include receiving at least one of an event associated with ending a function executed in the external device, an event associated with a communication disconnection with the external device, or an event associated with a change of the remaining capacity of a battery of the external device or the electronic device and deactivating the activated sensor based on the reception of the event.

According to various embodiments, the method may further include restoring a state of the sensor to a state before the external device connects with the electronic device in response to occurrence of the event.

According to various embodiments, the method may further include collecting context information, generating screen interface control information to be outputted on the external device based on the collected context information, and sending the screen interface control information to the external device.

According to various embodiments, the method may further include outputting an object for selecting at least one function executable in the external device on a sub-display module of the external device based on the context information.

According to various embodiments, the method may further include receiving specific function selection information from the external device and outputting at least one application selection item (e.g., an icon, a menu, and the like) associated with the received function selection information on a display module of the electronic device or automatically activating the at least one application selection item.

According to various embodiments, the collecting of the context information may include collecting at least one of weather information, location information, time information, season information, event information of a certain area, advertisement information, information associated with the remaining capacity of a battery of the external device, or information associated with a communication channel state with the external device based on the communication interface and collecting at least one of official anniversary information, personal anniversary information, personal schedule information or information associated with the remaining capacity of a battery of the electronic device, each of which is stored in a storage module of the electronic device.

According to various embodiments, the method may further include generating a state information table for at least one of a sensor of the electronic device, activated or deactivated by a request of the external device, or a sensor of the electronic device, activated or deactivated by a request of the electronic device and storing the state information table.

According to various embodiments, the method may further include updating the state information table, if the activation or deactivation of the sensor is changed by a request of the external device or a communication disconnection with the external device.

A device operation method based on request information according to various embodiments may include receiving request information from an external device communicably connected to an electronic device, activating a sensor of the electronic device based on the received request information, sending data generated based on the activated sensor to the external device, and deactivating the activated sensor if communication with the external device is disconnected and if a battery of the electronic device is low.

Figure 8:
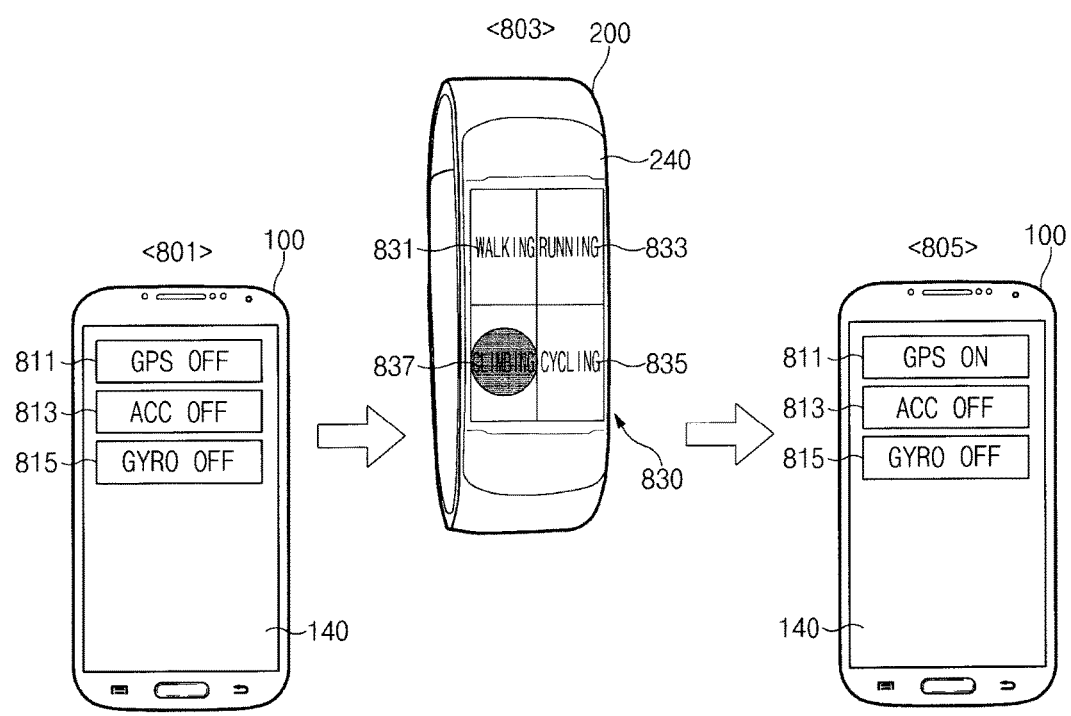
FIG. 8 is a drawing illustrating climbing mode related operation according to an embodiment.

FIG. 8 is a drawing illustrating climbing mode related operation according to an embodiment.

Referring to FIG. 8, in state 801, an electronic device 100 may maintain a GPS module in a turn-off state, may maintain an acceleration sensor in the turn-off state, and may maintain a gyro sensor in the turn-off state. Herein, in FIG. 8, an embodiment is exemplified as a screen in state 801 displays a GPS module item 811, an acceleration sensor item 813, and a gyro sensor item 815 are displayed on a display module 140. However, various embodiments are not limited thereto. For example, for understanding of states of the GPS module, the acceleration sensor, the gyro sensor, and the like, the screen in state 801 may display the GPS module item 811, the acceleration sensor item 813, and the gyro sensor item 815, and the displaying of the GPS module item 811, the acceleration sensor item 813, the gyro sensor item 815, and the like may be omitted based on a UI change.

If an event associated with an interworking function with an external device 200 is generated, the electronic device 100 may send specified UI control information to the external device 200. Herein, the event associated with the interworking function may include various events (e.g., an event for establishing a communication channel with the external device 200, an event for requesting to execute a specific application, an event for providing notification that the external device 200 executes a specific application, and the like). If the event associated with the interworking function is generated, the electronic device 100 may collect context information and may generate UI control information corresponding to the context information.

If receiving the UI control information from the electronic device 100, in state 803, the external device 200 may output a first UI screen 830 on a sub display module 240. The first UI screen 830 may include function items 831 to 837 associated with health coaching, for example, the walking item 831, the running item 833, the cycling item 835, and the climbing item 837. Therefore, the external device 200 may provide an environment in which the external device 200 immediately enters the first UI screen 830 upon being powered off or upon interworking with the electronic device 100. If one of the function items 831 to 837, for example, if the climbing item 831 is selected, the external device 200 may generate selection information. The external device 200 may send the selection information to the electronic device 100.

If receiving the selection information of the climbing item 831 from the external device 200, the electronic device 100 may control activation or deactivation of a specific device element in response to the selection information. For example, in state 805, the electronic device 100 may activate the GPS module. Therefore, the GPS module item 811 may be displayed as a turn-on state. The electronic device 100 may maintain an acceleration sensor and a gyro sensor in a deactivated state. Therefore, each of the acceleration sensor item 813 and the gyro sensor item 815 may be displayed as a turn-off state. In FIG. 8, an embodiment is exemplified as a screen in state 805 displays the GPS module item 811, the acceleration sensor item 813, and the gyros sensor item 815. However, various embodiments are not limited thereto. For example, the displaying of the items may be omitted based on a UI setting.

Figure 9:
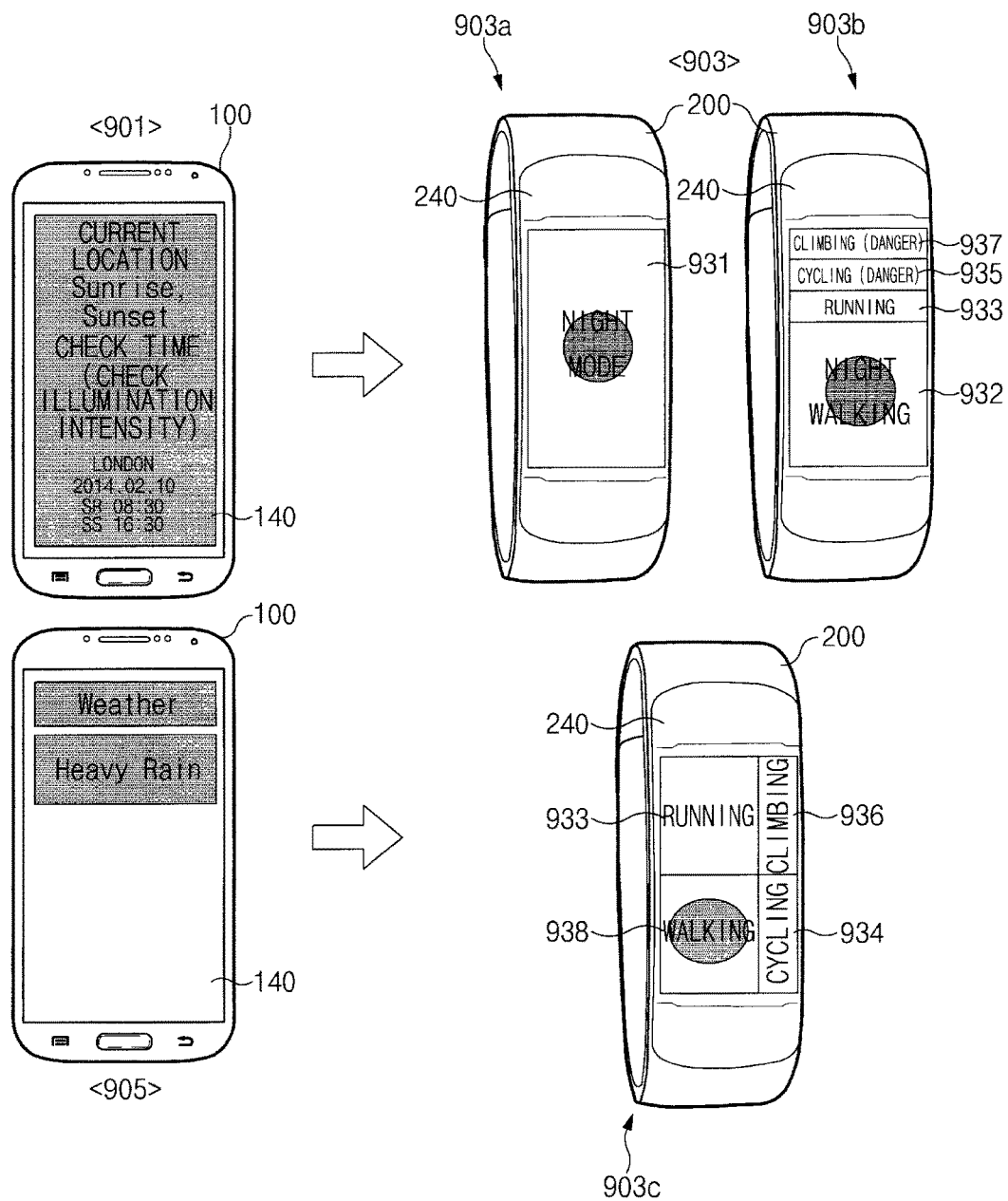
FIG. 9 is a drawing illustrating operation based on an environment around an electronic device according to an embodiment.

FIG. 9 is a drawing illustrating operation based on an environment around an electronic device according to an embodiment.

Referring to FIG. 9, in state 901, an electronic device 100 may collect a sensor signal of its illumination sensor as context information and may output the collected sensor signal on its display module 140. A control module 160 of FIG. 1 may analyze a sensor signal of the illumination sensor and may determine whether ambient conditions indicate night. In this operation, the control module 160 may collect current location information and sunrise/sunset time information in a current location. The control module 160 may analyze the sunrise/sunset time information and information of the illumination sensor in the current location and may extract information associated with a current state (e.g., night related information). The control module 160 may generate control information (e.g., UI control information corresponding to a night environment) based on the state related information. The control module 160 may send the control information to an external device 200.

If receiving control information associated with a night environment from the electronic device 100, in state 903, the external device 200 may output a screen corresponding to the control information on a sub display module 240. According to an embodiment, in state 903*a*, the external device 200 may output a screen including a night mode item 931 on the sub display module 240. According to an embodiment, in state 903*b*, the external device 200 may output a screen, on which a night walking item 932 has a larger size than other function items 933, 935, and 937, on the sub display module 240. In state 903*c*, the external device 200 may output a screen, on which a walking item 938 differs in color from other function items 933, 934, and 936, on the sub display module 240.

According to various embodiments, the external device 200 may output items unsuitable for night conditions in the form of not being recommended. For example, in state 903*b*, the external device 200 may output the climbing (danger) item 937 and the cycling (danger) item 935. The external device 200 may output the climbing (danger) item 937 and the cycling (danger) item 935 to have a different color or background from other function items 932 and 933. According to various embodiments, in state 903*c*, the external device 200 may output the running item 933 and the walking item 938 to have a different size or color from the other items 934 and 936. For example, the external device 200 may output the running item 933 and the walking item 938 to be larger in size than the other items 934 and 936. According to an embodiment, the external device 200 may change an order of items in response to control information and may output the changed items.

According to various embodiments, in state 905, the electronic device 100 may collect weather information as context information and may output the collected weather information on the display module 140. In this regard, the electronic device 100 may access a server device which provides weather information at a certain period (e.g., at intervals of one hour, 12 hours, one day, and the like) and may collect weather information of a current location or a specific location. The electronic device 100 may analyze the weather information and may generate control information corresponding to specific conditions (e.g., a rainstorm, a heavy rain, and the like). For example, if information associated with a rainstorm or heavy rain is included in weather information, the electronic device 100 may generate control information in a night state. Receiving the control information, the external device 200 may output one of screens in state 903.

Figure 10:
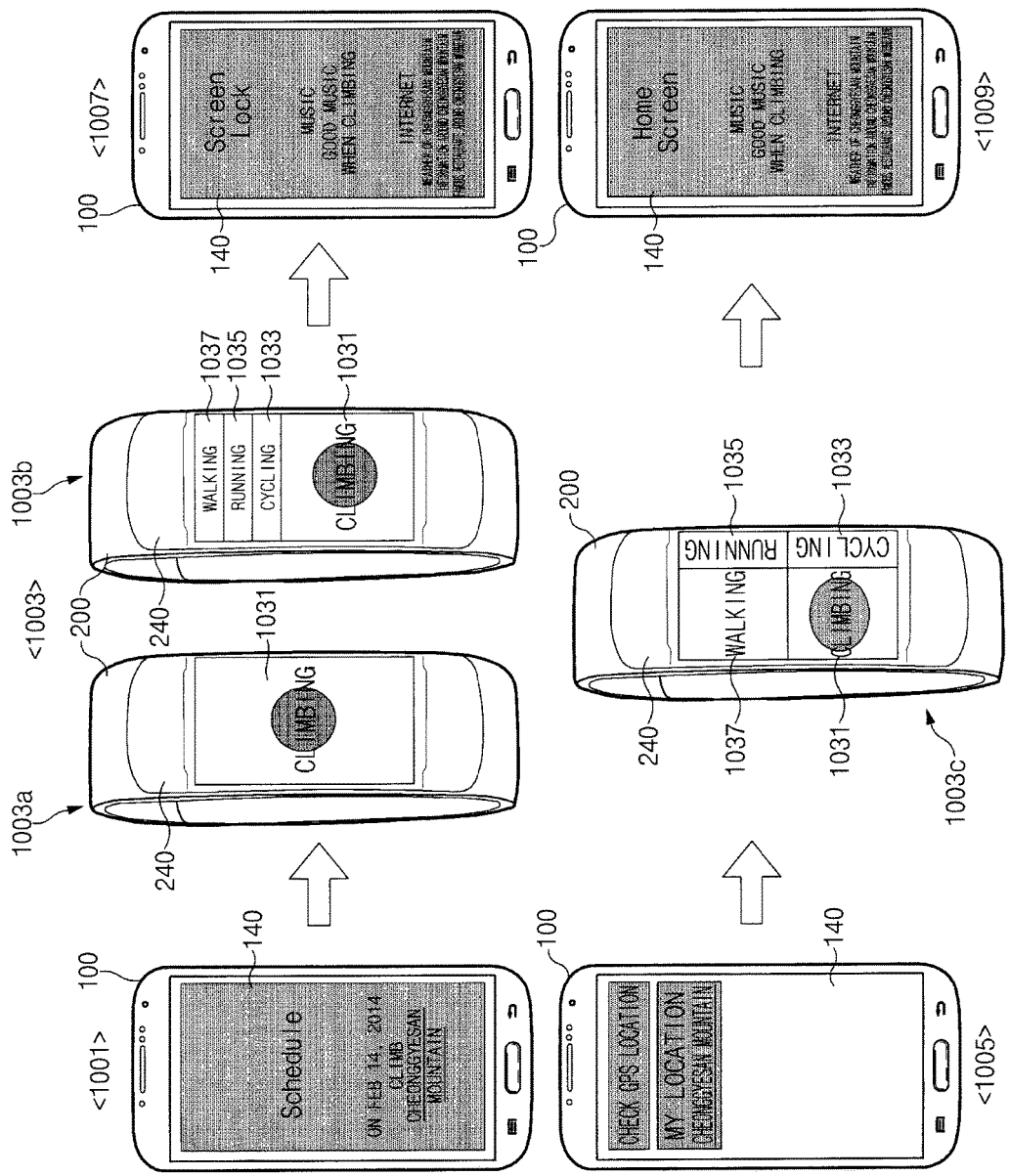
FIG. 10 is a drawing illustrating schedule related operation according to an embodiment.

FIG. 10 is a drawing illustrating schedule related operation according to an embodiment.

Referring to FIG. 10, an electronic device 100 may output schedule information, in which a time is specified, corresponding to context information in response to arrival of the corresponding time. In state 1001, a display module 140 may output schedule information in response to control of a control module 160 of FIG. 1. The control module 160 may generate control information based on collecting context information including the schedule information and may send the control information to an external device 200. In this regard, the control module 160 may extract state related information (e.g., climbing related information) from the schedule information. The control module 160 may generate control information corresponding to the extracted state related information. The control module 160 may establish a communication channel with the external device 200 and may send the control information to the external device 200. Herein, the control information may include UI control information corresponding to the state related information extracted from the schedule information.

If receiving the UI control information from the electronic device 100, in state 1003, the external device 200 may output a screen corresponding to the UI control information. According to an embodiment, in state 1003a, the external device 200 may output a screen including a climbing item 1031 on a sub display module 240. According to an embodiment, in state 1003b, the external device 200 may output a screen, on which the climbing item 1031 is arranged to differ in size from other function items 1033, 1035, and 1037, on the sub display module 240. According to an embodiment, in state 1003c, the external device 200 may output the climbing item 1031 on the sub display module 240 to have a different color from the other function items 1033, 1035, and 1037. If an event for selecting the climbing item 1031 is generated, the external device 200 may send selection information corresponding to the generated event to the electronic device 100.

According to various embodiments, the electronic device 100 may collect current location information using its GPS module. If the current location information indicates a specific area, for example, Cheonggyesan Mountain, in state 1005, the electronic device 100 may output the current location information on the display module 140. Herein, the electronic device 100 may output the current location information as coordinate information or a place name such as Cheonggyesan Mountain.

The electronic device 100 may collect the current location information as context information. If the current location is included in a specified location, for example, a mountain area, the electronic device 100 may generate control information corresponding to the current location. The electronic device 100 may send the generated control information to the external device 200. Therefore, as described above, the external device 200 may output the control information on the sub display module 240 of state 1003.

According to various embodiments, if specific schedule information is output based on arrival of a corresponding time in state 1001, the electronic device 100 may verify information written in the schedule information. For example, the electronic device 100 may extract information about "climbing" from the schedule information. If the information about "climbing" is extracted, the electronic device 100 may activate the GPS module and may collect current location information. If a current location is included in a mountain area of a specified location, the electronic device 100 may generate the above-mentioned control information and may send the generated control information to the external device 200. According to an embodiment, if the current location is included in an area except for a mountain, the electronic device 100 may omit to generate and send control information. The electronic device 100 may control a message output for requesting to verify schedule information.

According to various embodiments, in state 1005, the electronic device 100 may collect current location information. If the current location is included in a mountain area, in state 1001, the electronic device 100 may verify schedule information. If information associated with a "mountain" is included in the schedule information, the electronic device 100 may generate control information and may send the generated control information to the external device 200.

If receiving selection information from the external device 200, the electronic device 100 may perform a specific function corresponding to the selection information. For example, in state 1007, the electronic device 100 may perform a sound source play function and an Internet access function associated with the climbing item 1031. In this operation, the electronic device 100 may perform the sound source play function and the Internet access function through background processing in a state where a screen lock is set. The electronic device 100 may reproduce a climbing related sound source previously defined in connection with performing the sound source play function or may reproduce a sound source found through Internet search. Also, the electronic device 100 may collect information about a previously defined keyword, for example, weather information, ambient local information, restaurant information, and the like through an Internet search function. The electronic device 100 may the collected search information and the sound source play information on the display module 140. According to various embodiments, in state 1009, the electronic device 100 may output information about the sound source play function and the Internet access function on the display module 140 in a home screen state. States 1007 and 1009 are exemplified as the search information associated with Cheonggyesan Mountain and music reproduction associated with climbing.

Figure 11:
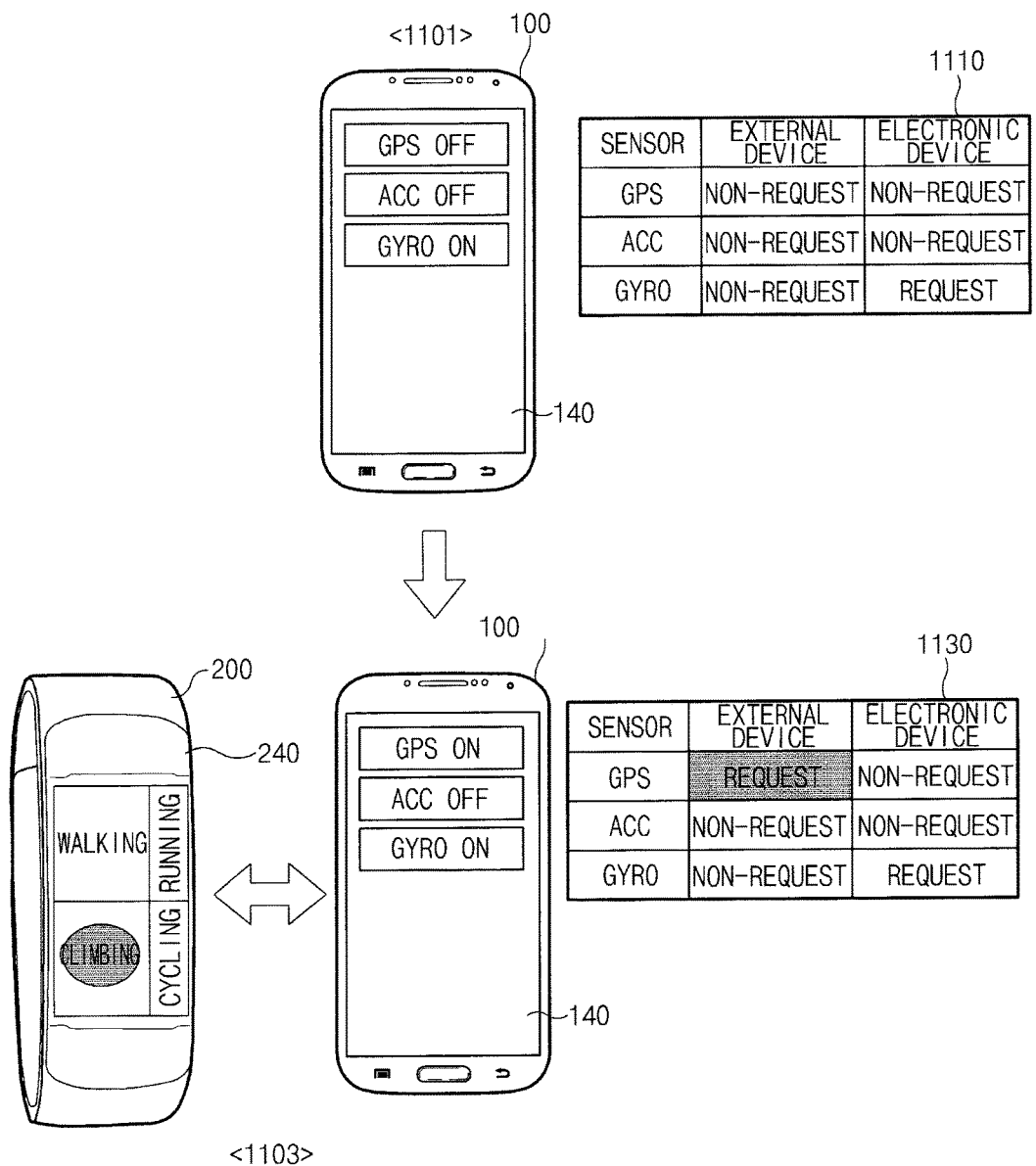
FIG. 11 is a drawing illustrating operation of a state control table associated with establishing a communication channel, according to an embodiment.

FIG. 11 is a drawing illustrating operation of a state control table associated with establishing a communication channel, according to an embodiment.

Referring to FIG. 11, an electronic device 100 may manage a state control table associated with a state of a device element in an interworking process with an external device 200. In this operation, the electronic device may assign and manage a flag in connection with a state change of a device element. According to an embodiment, before establishing a communication channel with the external device 200, in state 1101, the electronic device 100 may have a state where a GPS module is turned off, a state where an acceleration sensor is turned off, and a state where a gyro sensor is turned off. This state information may be output on a display module 140 of FIG. 1 or may be omitted to be output.

In response to states of device elements of the electronic device 100 in state 1101, the electronic device 100 may have a state control table 1110. The state control table 1110 may represent use states of the external device 200 and the electronic device 100 for the GPS module, the acceleration sensor, and the gyro sensor. For example, the state control table 1110 may have state information which is not requested to activate the GPS module, the acceleration sensor, and the gyro sensor from the external device 200 (or state information which is not requested to use the GPS module, the acceleration sensor, and the gyro sensor from the external device 200). The state control table 1110 may have state information which is not requested to activate the GPS module and the acceleration sensor from the electronic device 100. The state control table 1110 may have state information requested to activate the gyro sensor from a control module 160 of the electronic device 100.

According to an embodiment, in state 1103, the external device 10 and the electronic device 100 may establish a communication channel with each other. The electronic device 100 may generate UI control information in response to collecting context information and may send the generated control information to the external device 200. The external device 200 may output a screen corresponding to the UI control information on a sub display module 240 of FIG. 4. The external device 200 may send selection information corresponding to an event generated on at least one of the sub display module 240 or a sub input module 220 of FIG. 4 to the electronic device 100. In this operation, at least one of the external device 200 or the electronic device 100, for example, the external device 200 may request the electronic device 100 to activate the GPS module of the electronic device 100. In connection with interworking with the external device 200, in state 1103, the electronic device 100 may have a state where the GPS module is turned on, a state where the acceleration sensor is turned off, and a state where the gyro sensor is turned on. The electronic device 100 may output state information of the corresponding sensors on the display module 140 or may omit to output state information.

A state control table 1130 may have state information requested to activate the GPS module of the electronic device 100 from the external device 200. The state control table 1130 may have state information which is not requested to activate the acceleration sensor and the gyro sensor of the electronic device 100 from the external device 200. The state control table 1130 may have state information which is not requested to activate the GPS module and the acceleration sensor of the electronic device 100 from the control module 160 of the electronic device 100. The state control table 1130 may have state information requested to activate the gyro sensor of the electronic device 100 from the electronic device 100.

Figure 12:
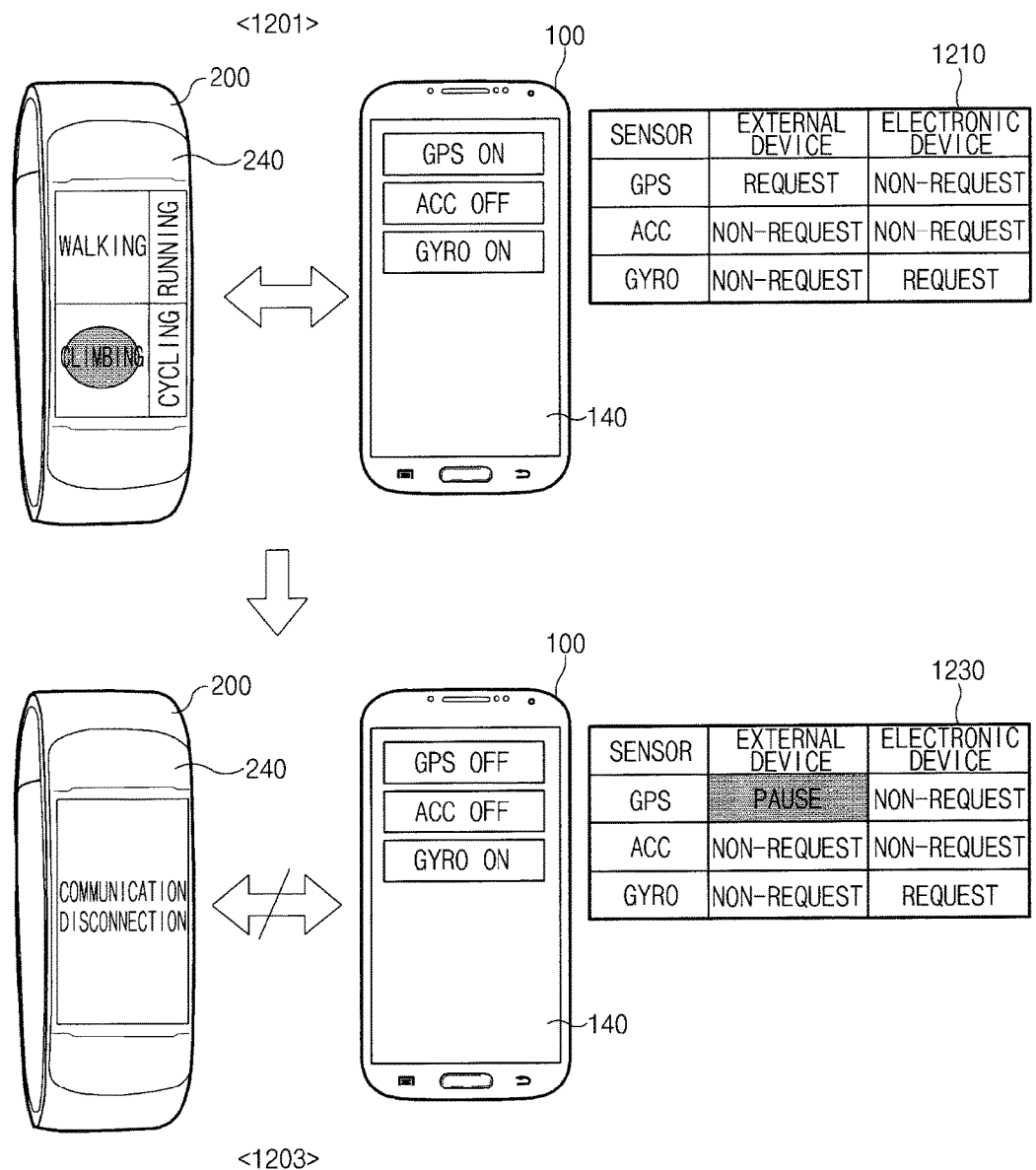
FIG. 12 is a drawing illustrating operation of a state control table associated with a disconnection according to an embodiment.

FIG. 12 is a drawing illustrating operation of a state control table associated with a disconnection according to an embodiment.

Referring to FIG. 12, an electronic device 100 may manage a state control table associated with a state of a device element in a communication disconnection process with an external device 200. For example, in state 1201, the electronic device 100 may have a state where its GPS module is turned on, a state where its acceleration sensor is turned off, and a state where its gyros sensor is turned on, in a process where a communication channel is established with the external device 200. This state information may be output on a display module 140 or may be omitted to be output. The electronic device 100 may have a state control table 1210 in response to states of device elements of the electronic device 100. The external device 200 may output a UI screen including at least one item on a sub display module 240 in response to a state where it is communicably connected with the electronic device 100.

The state control table 1210 may have state information requested to activate the GPS module from the external device 200 and state information which is not requested to activate the acceleration sensor and the gyro sensor from the external device 200. The state control table 1210 may have state information which is not requested to activate the GPS module and the acceleration sensor from the electronic device 100. The state control table 1210 may have state information requested to activate the gyro sensor from a control module 160 of the electronic device 100.

If communication between the electronic device 100 and the external device 200 is disconnected in state 1203, the electronic device 100 may change the GPS module from a turn-on state to a turn-off state. In this operation, the electronic device 100 may deactivate a communication module used for a communication connection between the electronic device 100 and the external device 200. The electronic device 100 may output information about a turn-on state or a turn-off state of each of its device elements on the display module 140. In state 1203, the external device may output information associated with a communication disconnection with the electronic device 100 on the sub display module 240.

In connection with the communication disconnection, a state control table 1230 may have state information requested to pause for the GPS module of the electronic device 100 from the external device 200. The state control table 1230 may have state information which is not requested to activate the acceleration sensor and the gyro sensor from the external device 200. The state control table 1230 may have state information which is not requested to activate the GPS module and the acceleration sensor of the electronic device 100 from the electronic device 100. The state control table 1230 may have state information which is not requested to activate the gyro sensor of the electronic device 100 from the external device 200, independent of the operation of the external device 200, and may have state information requested to activate the gyro sensor from the electronic device 100. According to various embodiments, if a communication disconnection state is maintained after a specified time elapses, the electronic device 100 may change the state information requested to pause for the GPS module to state information which is not requested to activate the GPS module.

Figure 13:
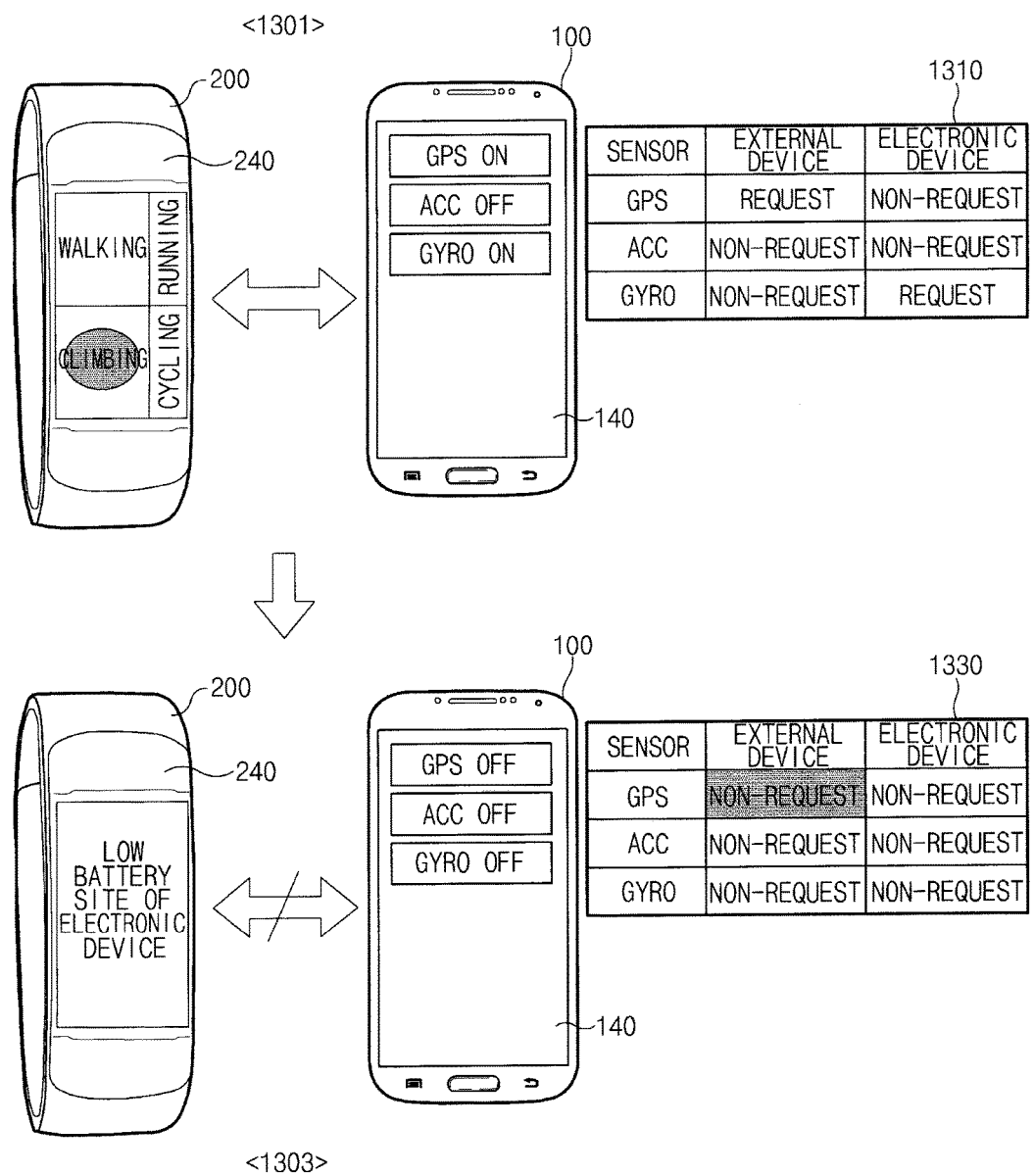
FIG. 13 is a drawing illustrating operation of a state control table associated with a low battery state of an electronic device, according to an embodiment.

FIG. 13 is a drawing illustrating operation of a state control table associated with a low battery state of an electronic device, according to an embodiment.

Referring to FIG. 13, as an electronic device 100 consumes its power based on operations of its device elements, it may have a power state of a specified value or less, for example, a low battery state. In this case, the electronic device 100 may disconnect communication with an external device.

According to an embodiment, before entering the low battery state, in state 1301, the electronic device 100 may have a state where its GPS module is turned on, a state where its acceleration sensor is turned off, and a state where its gyro sensor is turned on. State information of each device element may be output on a display module 140 or may be omitted to be output. Before entering the low battery state of the electronic device 100, the external device 200 may output a UI screen, including at least one item associated with interworking with the electronic device 100, on a sub display module 240.

Before entering the low battery state, in state 1301, the electronic device 100 may have a state control table 1310. The state control table 1310 may have state information requested to activate the GPS module from the external device 200 and state information which is not requested to activate the acceleration sensor and the gyro sensor from the external device 200. The state control table 1310 may have state information which is not requested to activate the GPS module and the acceleration sensor from the electronic device 100. The state control table 1310 may have state information requested to activate the gyro sensor from a control module 160 of the electronic device 160.

As the electronic device 100 enters the low battery state, in state 1303, it may disconnect communication with the external device 200. Before the communication disconnection, the electronic device 100 may send information about the low battery state of the electronic device 100 to the external device 200. In state 1303, the electronic device 100 may change the GPS module from a turn-on state to a turn-off state in response to entering the low battery state. Also, the electronic device 100 may change the gyro sensor from a turn-on state to a turn-off state in connection with the low battery state. In this operation, the electronic device 100 may deactivate a communication module used for a communication connection between the electronic device 100 and the external device 200. Before the communication disconnection, the external device 200 may receive information associated with entering the low battery state of the electronic device 100 from the electronic device 100. In state 1303, the external device 200 may output the information about the low battery state of the electronic device 100 on the sub display module 240.

The electronic device 100 may have a state control table 1330 in connection with entering the low battery state. The state control table 1330 may have state information which is not requested to activate the GPS module, the acceleration sensor, and the gyro sensor of the electronic device 100 from the external device 200. Also, the state control table 1330 may have state information which is not requested to activate the GPS module, the acceleration sensor, and the gyro sensor of the electronic device 100 from the electronic device 100. The electronic device 100 may deactivate the sensor module 170 and the GPS module in connection with entering the low battery state to minimize power consumption. In this state, the electronic device 100 may maintain mobile communication of 3 generation (3G)/4G in a waiting state.

Figure 14:
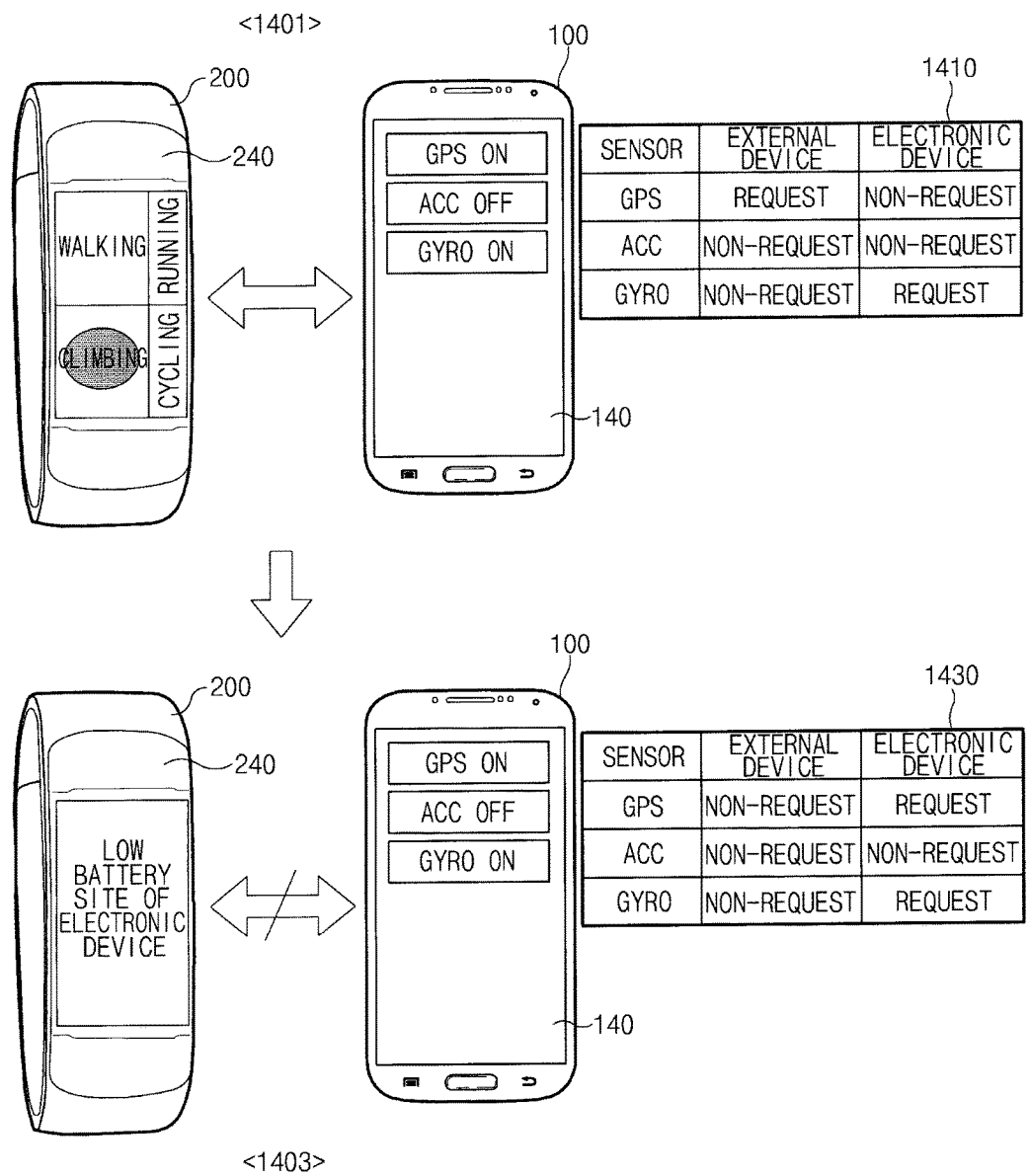
FIG. 14 is a drawing illustrating operation of a state control table associated with a low battery state of an external device, according to an embodiment.

FIG. 14 is a drawing illustrating operation of a state control table associated with a low battery state of an external device, according to an embodiment.

Referring to FIG. 14, in state 1401, an external device 200 may interwork with an electronic device 100 to support to perform a specific function. For example, the external device 200 may output a screen, including at least one item associated with health coaching based on execution of a health coaching function which interworks with the electronic device 100, on a sub display module 240. In connection with supporting a service based on the external device 200, the electronic device 100 may have a state where its GPS module is turned on, a state where its acceleration sensor is turned off, and a state where its gyro sensor is turned on. State information of each device element may be output on a display module 140 or may be omitted to be output. The electronic device 100 may have a state control table 1410 in response to a communication connection state.

The state control table 1410 may have state information requested to activate the GPS module from the external device 200 and state information which is not requested to activate the acceleration sensor and the gyro sensor from the external device 200. The state control table 1410 may have state information requested to activate the GPS module from the electronic device 100, state information which is not requested to activate the acceleration sensor from the electronic device 100, and state information requested to activate the gyro sensor from the electronic device 100.

As the external device 200 consumes its power based on operations of its device elements, it may have a power state of a specified value or less, for example, a low battery state. If entering the low battery state, in state 1403, the external device 200 may output information associated with entering the low battery state on the sub display module 240. If entering the low battery state, the external device 200 may send information associated with entering the low battery state to the electronic device 100. The electronic device 100 may disconnect communication with the external device 200 in connection with entering the low battery state of the external device 200.

As the external device 200 enters the low battery state, the electronic device 100 may disconnect communication with the external device 200. In connection with entering the low battery state of the external device 200, in state 1403, the electronic device 100 may have a state where the GPS module is turned on, a state where the acceleration sensor is turned off, and a state where the gyro sensor is turned on. In this operation, the electronic device 100 may deactivate a communication module used for a communication connection between the electronic device 100 and the external device 200.

The state control table 1430 may have state information which is not requested to activate the GPS module, the acceleration sensor, and the gyro sensor of the electronic device 100 from the external device 200. The state control table 1430 may have state information requested to activate the GPS module from the electronic device 100, state information which is not requested to activate the acceleration sensor from the electronic device 100, and state information requested to the gyro sensor from the electronic device 100. If communication is disconnected as the external device 200 enters the low battery state, the electronic device 100 may maintain device elements, activated in connection with operating the electronic device 100, in a turn-on state.

Figure 15:
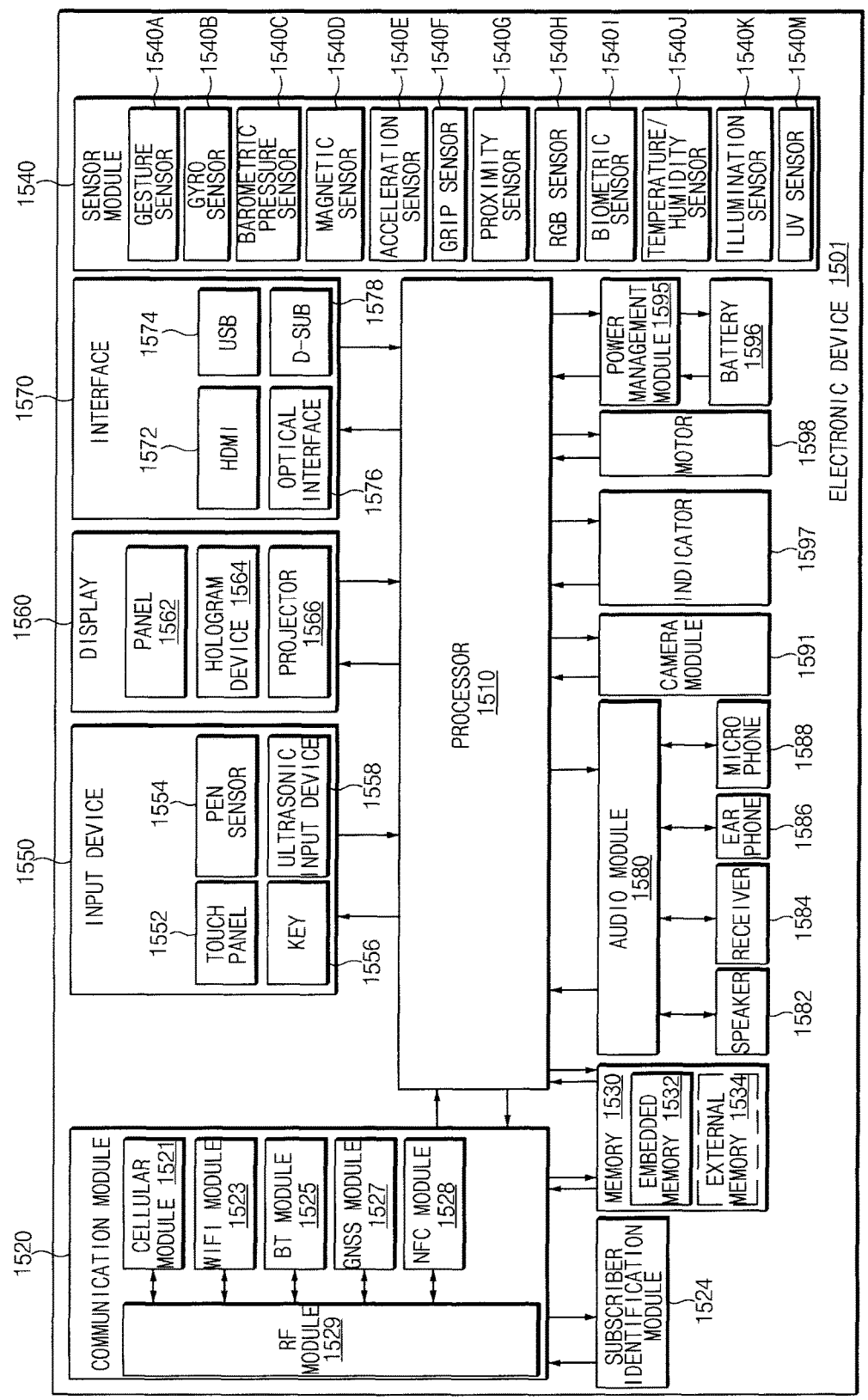
FIG. 15 is a block diagram illustrating a configuration of an electronic device according to another embodiments.

FIG. 15 is a block diagram illustrating a configuration of an electronic device according to various embodiments.

Referring to FIG. 15, an electronic device 1500 may include, for example, all or part of an electronic device shown in FIG. 1 or an external device 200 shown in FIG. 4. Referring to FIG. 15, the electronic device 1500 may include one or more application processors (APs) 1510, a communication module 1520, a subscriber identification module (SIM) card 1524, a memory 1530, a sensor module 1540, an input device 1550, a display 1560, an interface 1570, an audio module 1580, a camera module 1591, a power management module 1595, a battery 1596, an indicator 1597, and a motor 1598.

The AP 1510 may drive, for example, an operating system (OS) or an application program to control a plurality of hardware or software components connected thereto and may process and compute a variety of data including multimedia data. The AP 1510 may be implemented with, for example, a system on chip (SoC). According to an embodiment, the AP 1510 may include a graphic processing unit (GPU) (not shown).

According to an embodiment, various modules associated with processing the location related information may be implemented in the AP 1510. The AP 1510 may control related modules to collect and produce location information and to control function processing based on the collected or produced location information.

According to an embodiment, the various modules associated with processing the location related information may be divided and arranged in at least one of a communication processor (CP) or an AP. In this process, modules controlled by the CP may be arranged to perform direct communication with the CP in the same chipset, or hardware of the modules may be configured to connect with the CP through an external interface.

According to an embodiment, the various modules associated with processing the location related information may be disposed in the CP. Control of the related modules may be performed by the CP. In this case, a Wi-Fi module, a sensor hub, and a GPS module may be connected with the CP to perform direct communication. In this regard, the Wi-Fi module, the sensor hub, and the GPS module connect to a system bus in the same chipset and may connect to communicate with each other if the AP is in a power saving mode. If the Wi-Fi module, the sensor hub, and the GPS module are configured with different chipsets, the Wi-Fi module, the sensor hub, and the GPS module may connect through the external interface, hardware of which is configured to perform direct communication without passing through the AP.

The communication module 1520 may transmit and receive data in communication between other electronic devices connected with the electronic device 1500 (e.g., the electronic device 100 and the external device 200) through a network. The communication module 1520 may establish a communication channel with a server device and may receive context information from the server device. Also, the communication module 1520 may establish a communication channel with the external device 200. According to an embodiment, the communication module 1520 may include the cellular module 1521, a wireless-fidelity (Wi-Fi) module 1523, a Bluetooth (BT) module 1525, a global positioning system (GPS) module 1527, a near field communication (NFC) module 1528, and a radio frequency (RF) module 1529.

The cellular module 1521 may provide a voice call service, a video call service, a text message service, or an Internet service, and the like through a communication network (long term evolution (LTE), LTE-advanced (LTE-A), code division multiple access (CDMA), wideband CDMA (WCDMA), universal mobile telecommunications system (UMTS), wireless broadband (WiBro), or global system for mobile communications (GSM), and the like). Also, the cellular module 1521 may identify and authenticate, for example, the electronic device 1500 in a communication network using a SIM (e.g., the SIM card 1524). According to an embodiment, the cellular module 1521 may perform at least some of functions which may be provided by the AP 1510. For example, the cellular module 1521 may perform at least part of a multimedia control function.

According to an embodiment, the cellular module 1521 may include a communication processor (CP). Also, the cellular module 1521 may be implemented with, for example, a system on chip (SoC). In FIG. 15, an embodiment is exemplified as components such as the cellular module 1521 (e.g., the CP), the memory 1530, or the power management module 1595 and the like are independent of the AP 1510. However, according to an embodiment, the AP 1510 may be implemented to include at least some (e.g., the cellular module 1521) of the above-mentioned components.

According to an embodiment, the AP 1510 or the cellular module 1521 (e.g., the CP) may load a volatile memory with a command or data received from at least one of a non-volatile memory or another component connected thereto to process the command or data. Also, the AP or the cellular module 1521 may store data, received from at least one of other components or generated by at least one of the other components, in a non-volatile memory.

According to various embodiments, the cellular module 1521 may be included in a communication interface 130 described with reference to FIG. 1. The cellular module 1521 may establish a communication channel with the server device in a process of collecting context information of the electronic device 100. Also, the cellular module 1521 may collect ambient cell information in a process of producing location information of the electronic device 100.

The Wi-Fi module 1523, the BT module 1525, the GPS module 1527, or the NFC module 1528 may include, for example, a processor for processing data transmitted and received through the corresponding module. The Wi-Fi module 1523 and the BT module 1525 may be included in at least one of the communication interface 130 or a sub communication module 230 of FIG. 4. The GPS module 1527 may be included in the communication interface 130.

In FIG. 15, an embodiment is exemplified as the cellular module 1521, the Wi-Fi module 1523, the BT module 1525, the GPS module 1527, and the NFC module 1528 are independent of each other. However, according to an embodiment, at least some (e.g., two or more) of the cellular module 1521, the Wi-Fi module 1523, the BT module 1525, the GPS module 1527, or the NFC module 1528 may be included in one integrated chip (IC) or one IC package. For example, at least some of (e.g., a CP corresponding to the cellular module 1521 and a Wi-Fi processor corresponding to the Wi-Fi module 1523) of processors corresponding to the cellular module 1521, the Wi-Fi module 1523, the BT module 1525, the GPS module 1527, or the NFC module 1528 may be implemented with one SoC.

According to various embodiments, the Wi-Fi module 1523 may be included in the communication interface 130 described with reference to FIG. 1 and the sub communication module 230 described with reference to FIG. 4. As described above, the Wi-Fi module 1523 may establish a direct communication channel between the electronic device 100 and the external device 200. The Wi-Fi module 1523 may send at least one of state control information or UI control information from the electronic device 100 to the external device 200. The Wi-Fi module 1523 may send item selection information of the external device 200 to the electronic device 100.

The RF module 1529 may transmit and receive data, for example, a radio frequency (RF) signal. Though not shown, the RF module 1529 may include, for example, a transceiver, a power amplifier module (PAM), a frequency filter, or a low noise amplifier (LNA), and the like. Also, the RF module 1529 may further include a component, for example, a conductor or a conducting wire, for transmitting and receiving electromagnetic waves on free space in wireless communication. In FIG. 15, an embodiment is exemplified as the cellular module 1521, the Wi-Fi module 1523, the BT module 1525, the GPS module 1527, or the NFC module 1528 shares the one RF module 1529 with each other. However, according to an embodiment, at least one of the cellular module 1521, the Wi-Fi module 1523, the BT module 1525, the GPS module 1527, or the NFC module 1528 may transmit and receive an RF signal through a separate RF module.

The SIM card 1524 may include, for example, a card which includes a SIM and may be inserted into a slot formed in a specific location of the electronic device 1500. The SIM card 1524 may include unique identification information (e.g., an integrated circuit card identifier (ICCID)) or subscriber information (e.g., an international mobile subscriber identity (IMSI)). According to an embodiment, the SIM card 1524 may be part of a memory device. If the SIM card 1524 is inserted into the slot, the AP 1510 may perform an initialization process of the SIM card 1524.

The memory 1530 (e.g., a storage module 150 of FIG. 1 or a sub storage module 250 of FIG. 4) may include, for example, an embedded memory 1532 or an external memory 1534. The embedded memory 1532 may include at least one of, for example, a volatile memory (e.g., a dynamic random access memory (DRAM), a static RAM (SRAM), a synchronous dynamic RAM (SDRAM), and the like), or a non-volatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a NAND flash memory, a NOR flash memory, and the like). According to an embodiment, the embedded memory 1532 may be a solid state drive (SSD).

The external memory 1534 may include a flash drive, for example, a compact flash (CF), a secure digital (SD), a micro-SD, a mini-SD, an extreme digital (xD), or a memory stick, and the like. The external memory 1534 may operatively connect with the electronic device 1500 through various interfaces. According to an embodiment, the electronic device 1500 may further include a storage device (or a storage medium) such as a hard drive.

The sensor module 1840 may measure a physical quantity or may detect an operation state of the electronic device 1500, and may convert the measured or detected information to an electric signal. The sensor module 1540 may include at least one of, for example, a gesture sensor 1540A, a gyro sensor 1540B, a barometric pressure sensor 1540C, a magnetic sensor 1540D, an acceleration sensor 1540E, a grip sensor 1540F, a proximity sensor 1540G, a color sensor 1540H (e.g., red, green, blue (RGB) sensor), a biometric sensor 1540I, a temperature/humidity sensor 1540J, an illumination sensor 1540K, or an ultraviolet (UV) sensor 1540M. Additionally or alternatively, the sensor module 1540 may include, for example, an e-nose sensor (not shown), an electromyography (EMG) sensor (not shown), an electroencephalogram (EEG) sensor (not shown), an electrocardiogram (ECG) sensor (not shown), an infrared (IR) sensor (not shown), an iris sensor (not shown), and/or a fingerprint sensor (not shown), and the like. The sensor module 1540 may further include a control circuit for controlling at least one or more sensors included therein.

According to various embodiments, the sensor module 1540 may collect a sensor signal associated with an operation of the electronic device 1500 and a sensor signal associated with ambient conditions. The sensor signal collected by the sensor module 1540 may be sent to the AP 1510. The AP 1510 may process the sent sensor signal as context information. At least one sensor included in the sensor module 1540 may be activated in connection with operating the external device 200. If communication with the external device 200 is disconnected or if it is impossible to operate the external device 200, the at least one sensor included in the sensor module 1540 may be deactivated. In this operation, the sensor activated in connection with operating the electronic device 100 may maintain an activated state, if it is impossible to operate the external device 200.

The input device 1550 may include a touch panel 1552, a (digital) pen sensor 1554, a key 1556, or an ultrasonic input unit 1558. The input device 1550 may include at least one of an input and output module 120 described with reference to FIG. 1 or a sub input module 220 described with reference to FIG. 4.

The touch panel 1552 may recognize, for example, a touch input using at least one of a capacitive type, a resistive type, an infrared type, or an ultrasonic type. Also, the touch panel 1552 may include a control circuit. In case of the capacitive type, the touch panel 1552 may recognize a physical contact or may perform proximity recognition. The touch panel 1552 may further include a tactile layer. In this case, the touch panel 1552 may provide a tactile reaction to a user. The touch panel 1552 may generate a touch event associated with executing a specific function using location related information. According to an embodiment, the touch panel 1522 may activate or deactivate an automatic screen conversion function and may generate a touch event for selecting a type of a function to be applied to the automatic screen conversion function.

The (digital) pen sensor 1554 may be implemented using the same or similar method to a method of receiving a touch input of the user or a separate sheet for recognition. The key 1556 may include, for example, a physical button, an optical key, or a keypad. The ultrasonic input unit 1558 may allow the electronic device 1500 to detect a sound wave using a microphone (e.g., a microphone 1588) and to verify data through an input tool which generates an ultrasonic signal, and may perform wireless recognition. According to an embodiment, the electronic device 1500 may receive a user input from an external device (e.g., a computer or a server) connected with the communication module 1520, using the communication module 1520.

The display 1560 (e.g., a display module 140 of FIG. 1 or a sub display module 240 of FIG. 4) may include a panel 1562, a hologram device 1564, or a projector 1566. The panel 1562 may be, for example, a liquid-crystal display (LCD), an active-matrix organic light-emitting diode (AM-OLED), and the like. The panel 1662 may be implemented to be, for example, flexible, transparent, or wearable. The panel 1562 and the touch panel 1552 may be integrated into one module. The hologram device 1564 may show a stereoscopic image in a space using interference of light. The projector 1566 may project light onto a screen to display an image. The screen may be positioned, for example, inside or outside the electronic device 1500. According to an embodiment, the display 1560 may further include a control circuit for controlling the panel 1562, the hologram device 1564, or the projector 1566.

The interface 1570 may include, for example, a high-definition multimedia interface (HDMI) 1572, a universal serial bus (USB) 1574, an optical interface 1576, or a D-subminiature 1578. Additionally or alternatively, the interface 1570 may include, for example, a mobile high definition link (MEL) interface, an SD card/multimedia card (MMC) interface, or an infrared data association (IrDA) standard interface.

The audio module 1580 (e.g., an input and output module 120 of FIG. 1) may interchangeably convert a sound into an electric signal. The audio module 1580 may process sound information input or output through, for example, a speaker 1582, a receiver 1584, an earphone 1586, or the microphone 1588, and the like. According to an embodiment, the audio module 1580 arranged in the external device 200 may output audio data sent from the electronic device 100.

The camera module 1591 may be a device which captures a still image and a moving image. According to an embodiment, the camera module 1591 may include one or more image sensors (not shown) (e.g., a front sensor or a rear sensor), a lens (not shown), an image signal processor (ISP) (not shown), or a flash (not shown) (e.g., an LED or a xenon lamp).

The power management module 1595 may manage power of the electronic device 1500. According to an embodiment, the power management module 1595 control the power supply to at least one of device elements of the electronic device 1500. For example, if the power of the battery 1596 of the electronic device 1500 is less than or equal to a setting or less, the power management module 1595 may interrupt the power supply to a specific device element (e.g., a sensor module 170 of FIG. 1, a communication module which establishes a direct communication channel, a GPS module, and the like). The power management module 1595 may interrupt the power supply to device elements activated in connection with operating the external device 200 based on a communication disconnection with the external device 200 or a low battery state of the external device 200, and the like. Though not shown, the power management module 1595 may include a power management integrated circuit (PMIC), a charger IC or a battery or fuel gauge.

The PMIC may be mounted on, for example, an integrated circuit (IC) or a system on chip (SoC). A charging method may be classified into a wired charging method and a wireless charging method. The charger IC may charge the battery 1596 and may prevent overvoltage or overcurrent from flowing from a charger. According to an embodiment, the charger IC may include a charger IC for at least one of the wired charging method or the wireless charging method. The wireless charging method may include, for example, a magnetic resonance method, a magnetic induction method, or an electromagnetic method, and the like. An additional circuit for wireless charging, for example, a coil loop, a resonance circuit, or a rectifier, and the like may be further provided.

The battery gauge may measure, for example, the remaining capacity of the battery 1596 and voltage, current, or temperature thereof while the battery 1596 is charged. The battery 1596 may store or generate electricity and may supply power to the electronic device 1500 using the stored or generated electricity. The battery 1596 may include, for example, a rechargeable battery or a solar battery.

The indicator 1597 may display a specific state of the electronic device 1500 or part (e.g., the AP 1510) thereof, for example, a booting state, a message state, or a charging state, and the like. According to an embodiment, the indicator 1597 may display a communication connection state with the external device 200. The motor 1598 may convert an electric signal into mechanical vibration. Though not shown, the electronic device 1500 may include a processing unit (e.g., a GPU) for supporting a mobile TV. The processing unit for supporting the mobile TV may process media data according to standards, for example, a digital multimedia broadcasting (DMB) standard, a digital video broadcasting (DVB) standard, or a mediaFlo™ standard, and the like.

Figure 16:
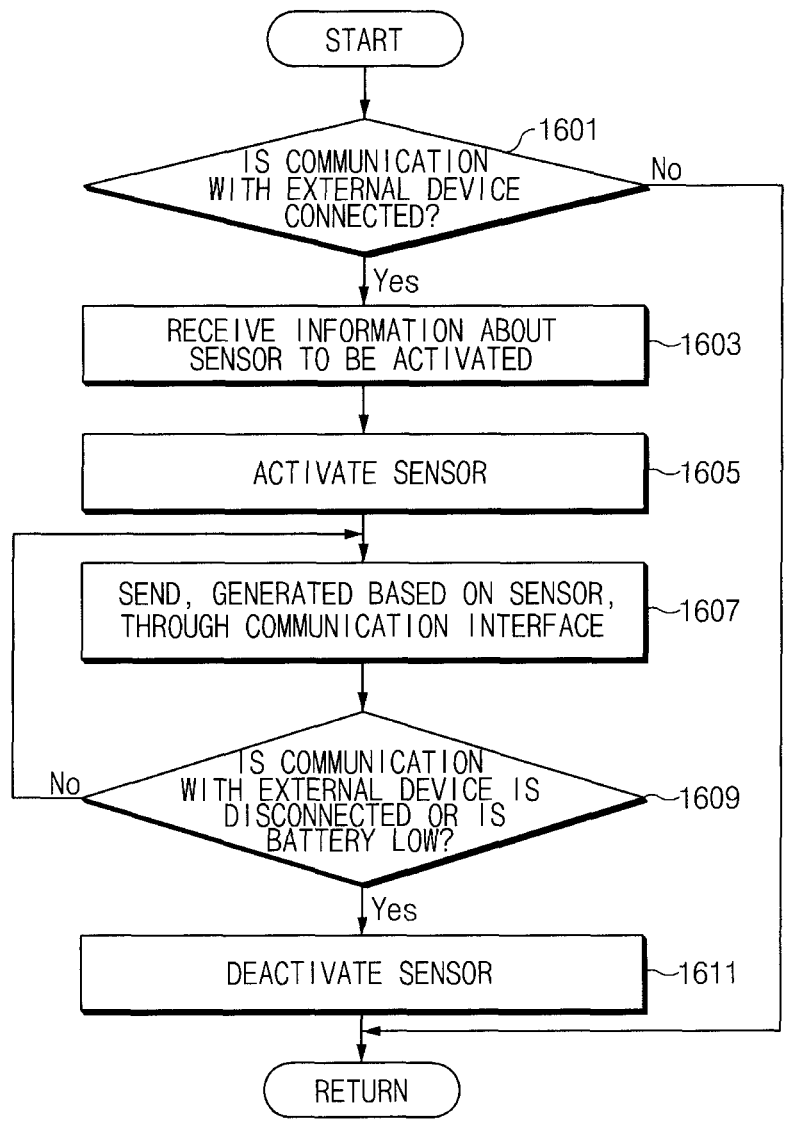
FIG. 16 is a flowchart illustrating a device operation method based on request information according to various embodiments. Throughout the drawings, it should be noted that like reference numbers are used to depict the same or similar elements, features, and structures.

FIG. 16 is a flowchart illustrating a device operation method based on request information according to various embodiments.

Referring to FIG. 16, in operation 1610 of the device operation method, an electronic device 100 of FIG. 1 may determine whether an event associated with a request for a communication connection with an external device 200 of FIG. 1 is generated. For example, the electronic device 100 may determine whether a message associated with a communication connection request is received from the external device 200. Alternatively, the electronic device 100 may determine whether there is an input event or schedule information for requesting a communication connection with the external device 200.

If the event associated with the request for the communication connection with the external device 200 is generated in operation 1601, the electronic device 100 may process a communication connection based on the corresponding event. For example, the electronic device 100 may establish a direct communication channel with the external device 200 using at least one communication module included in a communication interface 130 of FIG. 1.

In operation 1603, the electronic device 100 may receive information about a sensor to be activated, from the external device 200. In this regard, if receiving a request associated with executing a specific function in a state where a communication channel is established with the electronic device 100, the external device 200 may determine whether a sensor which supports to execute the corresponding function is included in the external device 200. The sensor associated with executing the specific function is not included in the external device 200, the electronic device 100 may send information, about a sensor which requests the electronic device 100 to execute the corresponding function in connection with executing the corresponding function, to the electronic device 100.

If receiving sensor information including information of sensors requested to execute the corresponding function from the external device 200, the electronic device 100 may activate the sensors based on the corresponding information. For example, the electronic device 100 may receive sensor information corresponding to a request to activate a GPS module from the external device 200. The electronic device 100 may activate the GPS module in response to an activation request of the external device 200.

In operation 1607, the electronic device 100 may send data generated based on the sensor through the communication interface 130. For example, the electronic device 100 may send a sensor signal collected by the GPS module requested to be activated by the external device 200 to the external device 200. In this operation, the electronic device 100 may send a sensor signal collected by a specific sensor to the external device 200 without change, or may process the sensor signal in response to executing a function of the external device 200 and may send the processed sensor signal to the external device 200. According to an embodiment, if a function executed in the external device 200 is a climbing function, the electronic device 100 may send a sensor signal collected by the GPS module together with map information within an ambient certain range relative to a current location to the external device 200. According to an embodiment, the electronic device 100 may analyze a movement speed of the external device 200 and may adjust a transmission period of a sensor signal collected in real time by the GPS module in a different way. According to an embodiment, the electronic device 100 may send only part of information collected by the GPS module based on properties of a function executed in the external device 200. For example, the electronic device 100 may calculate a location corresponding to accuracy of a function executed in the external device 200 from information collected by the GPS module and may send information about the location corresponding to the corresponding accuracy to the external device 200.

In operation 1609, the electronic device 100 may determine whether communication with the external device 200 is disconnected or a battery (e.g., at least one of a battery of the electronic device 100 or a battery of the external device 200) is low. If the communication with the external device 200 is not disconnected or if the battery is not low in operation 1609, the electronic device 100 may perform operation 1607.

If the communication with the external device 200 is disconnected or if the battery is low in operation 1609, the electronic device 100 may branch to operation 1611 to deactivate the sensor. In this operation, the electronic device 100 may deactivate the sensors requested to be activated by the external device 200. If the sensors activated by the external device 200 are requested to be activated by the control module 160, the electronic device 100 may control the sensors to maintain activation under control of the electronic device 100. If a sensor activated in response to ending an interworking function with the external device 200 is deactivated, the electronic device 100 may update a state information table.

Additionally or alternatively, if receiving an event associated with ending a currently executed function from the external device 200, the electronic device 100 may branch to operation 1611. Additionally or alternatively, if an event associated with releasing or ending an interworking function with the external device 200 is generated from an input and output module 120 of FIG. 1, the electronic device 100 may end interworking function which is being executed between the electronic device 100 and the external device 200 to branch to operation 1611.

As described above, in the device operation method and the device for supporting the same according to an embodiment, the electronic device 100 may determine context information (e.g., a schedule, a user location, and the like), may adaptively change screen elements (e.g., an object or item output on a screen, a background screen, arrangement of objects, and the like) of the sub display module 240 of the external device 200 based on the information, and may allow the user to easily select a function in the external device 200.

Also, in the device operation method and the device for supporting the same according to various embodiments, if a sensor associated with supporting a function (e.g., a function based on selection of a specific object or item displayed in connection with executing the function on a menu screen) selected on the sub display module 240 of the external device 200 is included in the electronic device 100, the external device 200 may request the electronic device 100 to activate the corresponding sensor, may receive a sensor signal from the electronic device 100, and may support to execute the function. Herein, if the sensor associated with executing the specific function is arranged in all of the external device 200 and the electronic device 100, the external device 200 may use the sensor of the electronic device 100 based on a default setting. Additionally or alternatively, in the device operation method and the device for supporting the same according to an embodiment, the external device 200 may operate the sensor arranged in the external device 200 based on a state of the remaining capacity of the battery in at least one of a state where the remaining capacity of the battery of the electronic device 100 is less than or equal to a certain level or a state where the remaining capacity of the battery of the external device 200 is greater than or equal to the certain level.

Also, in the device operation method and the device for supporting the same according to various embodiments, the electronic device 100 may restore a state of the electronic device 100 to a state before it interworks with the external device 200 in response to at least one of a state where a specific function of the external device 200 is ended, a state where communication with the external device 200 is disconnected, or a state where the remaining capacity of the battery of at least one of the electronic device 100 or the battery of the external device 200 is less than or equal to a certain level. For example, if communication with the external device 200 is disconnected, the electronic device 100 may restore a state of a sensor activated by the request of the external device 200 to a state based on a setting of the electronic device 100.

In the device operation method and the device for supporting the same according to various embodiments, the electronic device 100 may recommend at least one function (application) to be executed in the electronic device 100 in connection with a function selected in the external device 200. For example, if a climbing function is selected in the external device 200, the electronic device 100 may automatically execute a sound source play application and a web access function in connection with the climbing function or may output function selection information on the display module 140 if receiving the function selection information of the external device 200 to easily select execution of the function.

Each of the above-mentioned elements of the electronic device according to various embodiments of the present disclosure may be configured with one or more components, and names of the corresponding elements may be changed according to the type of the electronic device. The electronic device according to various embodiments of the present disclosure may include at least one of the above-mentioned elements, some elements may be omitted from the electronic device, or other additional elements may be further included in the electronic device. Also, some of the elements of the electronic device according to various embodiments of the present disclosure may be combined with each other to form one entity, thereby making it possible to perform the functions of the corresponding elements in the same manner as before the combination.

The terminology "module" used herein may mean, for example, a unit including one of hardware, software, and firmware or two or more combinations thereof. The terminology "module" may be interchangeably used with, for example, terminologies "unit", "logic", "logical block", "component", or "circuit", and the like. The "module" may be a minimum unit of an integrated component or a part thereof. The "module" may be a minimum unit performing one or more functions or a part thereof. The "module" may be mechanically or electronically implemented. For example, the "module" may include at least one of an application-specific integrated circuit (ASIC) chip, field-programmable gate arrays (FPGAs), or a programmable-logic device, which is well known or will be developed in the future, for performing certain operations.

According to various embodiments, at least part of a device (e.g., modules or the functions) or a method (e.g., operations) may be implemented with, for example, instructions stored in computer-readable storage media in the form of a program module. When the instructions are executed by one or more processors (e.g., a control module 160 of FIG. 1), the one or more processors may perform functions corresponding to the instructions. The computer-readable storage media may be, for example, a storage module 150 of FIG. 1. At least part of the programming module may be implemented by, for example, the control module 160. At least part of the programming module may include, for example, a module, a program, a routine, sets of instructions, or a process, for performing one or more functions.

The computer-readable storage media may include magnetic media such as a hard disc, a floppy disk, and a magnetic tape; optical media such as a compact disc read only memory (CD-ROM) and a digital versatile disc (DVD); magneto-optical media such as a floptical disk); a hardware device, such as a ROM, a random access memory (RAM), and a flash memory, specially configured to store and perform program instructions (e.g., a program module). Also, the program instructions may include not only mechanical codes compiled by a compiler but also high-level language codes which may be executed by a computer using an interpreter and the like. The above-mentioned hardware device may be configured to operate as one or more software modules to perform operations according to various embodiments of the present disclosure, and vice versa.

Modules or program modules according to various embodiments of the present disclosure may include at least one or more of the above-mentioned components, some of the above-mentioned components may be omitted, or other additional components may be further included. Operations executed by modules, program modules, or other components may be executed by a successive method, a parallel method, a repeated method, or a heuristic method. Also, some operations may be executed in a different order or may be omitted, and other operations may be added.

The expressions "include", "comprise", "including", or "comprising" used herein indicates existence of corresponding functions, operations, or elements but does not exclude one or more additional functions, operations, or elements. Also, in various embodiments, it should be understood that the term "include", "comprise", "have", "including", "comprising", or "having" used herein specifies the presence of features, integers, operations, elements, components, or combinations thereof but does not preclude the presence or addition of one or more other features, integers, operations, elements, components, or combinations thereof.

The expression "or" and the like used in various embodiments includes any combination of words listed together with the term. For example, the expression "A or B" may include A, B, or both A and B.

The expressions such as "1st", "2nd", "first", or "second", and the like used in various embodiments may refer to various elements of various embodiments, but do not limit the elements. For example, such terms do not limit the order and/or priority of the elements. The expressions may be used to distinguish one element from another element. For example, without departing from the scope of the present disclosure, a first element may be referred to as a second element, and similarly, a second element may be referred to as a first element.

It will be understood that when an element is referred to as being "connected" or "coupled" to another element, it can be directly connected or coupled to the other element or intervening elements may be present. In contrast, when an element is referred to as being "directly connected" or "directly coupled" to another element, it should be understood that there are no intervening elements.

Terms used in various embodiments are used to describe specified embodiments of the present disclosure and are not intended to limit the scope of the present disclosure. The terms of a singular form may include plural forms unless otherwise specified.

Unless otherwise defined herein, all the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal detect unless expressly so defined herein in various embodiments of the present disclosure. In some cases, even if terms are terms which are defined in the specification, they may not be interpreted to exclude embodiments of the present disclosure.

Electronic devices according to various embodiments may be devices which support to process location information. For example, electronic devices may include at least one of, for example, smartphones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, mobile medical devices, cameras, or wearable devices (e.g., smart glasses, head-mounted-devices (HMDs), an electronic apparel, electronic bracelets, electronic necklaces, electronic appcessories, electronic tattoos, smart mirrors, or smart watches).

According to various embodiments, the electronic devices may be smart home appliances which support to process location information. The smart home appliances may include at least one of, for example, televisions (TVs), digital versatile disk (DVD) players, audios, refrigerators, air conditioners, cleaners, ovens, microwave ovens, washing machines, air cleaners, set-top boxes, home automation control panels, security control panels, TV boxes (e.g., Samsung HomeSync™, Apple TV™, or Google TV™), game consoles (e.g., Xbox™ and PlayStation™), electronic dictionaries, electronic keys, camcorders, or electronic picture frames.

According to various embodiments, the electronic devices may include at least one of various medical devices (e.g., various portable medical measurement devices (e.g., blood glucose meters, heart rate meters, blood pressure meters, or thermometers, and the like), a magnetic resonance angiography (MRA), a magnetic resonance imaging (MRI), a computed tomography (CT), scanners, or ultrasonic devices, and the like), navigation devices, global navigation satellite system (GNSS), event data recorders (EDRs), flight data recorders (FDRs), vehicle infotainment devices, electronic equipment for vessels (e.g., navigation systems, gyrocompasses, and the like), avionics, security devices, head units for vehicles, industrial or home robots, automatic teller's machines (ATMs), points of sales (POSs), or internet of things (e.g., light bulbs, various sensors, electric or gas meters, sprinkler devices, fire alarms, thermostats, street lamps, toasters, exercise equipment, hot water tanks, heaters, boilers, and the like).

According to various embodiments, the electronic devices may include at least one of parts of furniture or buildings/structures, electronic boards, electronic signature receiving devices, projectors, or various measuring instruments (e.g., water meters, electricity meters, gas meters, or wave meters, and the like), each of which supports to process location information. The electronic devices according to various embodiments of the present disclosure may be one or more combinations of the above-mentioned devices. The electronic devices according to various embodiments of the present disclosure may be flexible electronic devices. Also, electronic devices according to various embodiments of the present disclosure are not limited to the above-mentioned devices, and may include new electronic devices according to technology development Embodiments of the present disclosure described and shown in the drawings are provided as examples to describe technical content and help understanding but do not limit the scope of the present disclosure. Accordingly, it should be interpreted that besides the embodiments listed herein, all modifications or modified forms derived based on the technical ideas of the present disclosure are included in the scope of the present disclosure as defined in the claims, and their equivalents.

What is claimed is:
1. An electronic device, comprising:
a communication interface configured to establish a communication channel with an external wearable device;
a plurality of sensors; and
a processor configured to:

generate screen control information based on collected context information, transmit, by the communication interface, the generated screen control information to the external wearable device, such that the external wearable device displays a menu based on the transmitted screen control information, wherein the menu includes a plurality of icons selectable on the external wearable device and respectively corresponding to a plurality of user's activities, and receive, by the communication interface from the external wearable device, selection information corresponding to a selected icon from among one or more icons included in the menu, and control at least one sensor of the plurality of sensors to be activated based on the received selection information, wherein the plurality of user's activities includes at least one of walking, running, cycling, and climbing.

2. The electronic device of claim 1, wherein the processor is configured to send at least part of a sensor signal collected by the activated sensor and at least one of signals processed based on the sensor signal to the external device, and wherein a preset activation configuration includes activation of at least one sensor of the external wearable device, such that the one or more icons are selectable to simultaneously control activation of sensors of both the electronic device and the external wearable device.

3. The electronic device of claim 1, wherein the processor is configured to deactivate the activated sensor based on at least one of an event associated with ending a function executed in the external device, an event associated with a communication disconnection with the external device, or an event associated with a change of the remaining capacity of a battery of the external device or the electronic device.

4. The electronic device of claim 1, wherein the processor is configured to restore a state of the sensor to a previous state based on at least one of an event associated with ending a function executed in the external device, an event associated with a communication disconnection with the external device, or an event associated with a change of the remaining capacity of a battery of the external device or the electronic device.

5. The electronic device of claim 1, wherein the sensor is a location sensor, and the processor is configured to generate the menu based at least in part on location information obtained from the location sensor.

6. The electronic device of claim 1, wherein the processor is configured to collect context information including sensor information, and at least one of weather information, location information, time information, season information, event information of an area, advertisement information, information about the remaining capacity of a battery of the external device, or information about a communication channel state with the external device based on the communication interface or at least one of official anniversary information, personal anniversary information, personal schedule information or information about the remaining capacity of a battery of the electronic device, each of which is stored in a storage module of the electronic device.

7. The electronic device of claim 1, wherein the processor is configured to generate a state information table for at least one of a sensor of the electronic device, activated or deactivated by a request of the external device, or a sensor of the electronic device, activated or deactivated by a request of the electronic device.

8. The electronic device of claim 7, wherein, in response to the activation or deactivation of the sensor being changed by a request of the external device or a communication disconnection with the external device, the processor is configured to update the state information table.

9. A method in an electronic device, comprising:

establishing, by the electronic device, a communication channel with an external wearable device;

generating screen control information based on collected context information;

transmitting, by a communication interface, the generated screen control information to the external wearable device such that the external wearable device displays a menu based on the transmitted screen control information, wherein the menu includes a plurality of icons selectable on the external wearable device and respectively corresponding to a plurality of user's activities;

receive, by the communication interface from the external wearable device, selection information corresponding to a selected icon from among one or more icons included in the menu; and control at least one sensor of a plurality of sensors to be activated based on the received selection information, wherein the plurality of user's activities includes at least one of walking, running, cycling, and climbing.

10. The method of claim 9, further comprising:

sending, by the electronic device, at least part of a sensor signal collected by the activated sensor and at least one of signals processed based on the sensor signal to the external device, and wherein a preset activation configuration further includes activation of at least one sensor of the external wearable device, such that the one or more icons are selectable to simultaneously control activation of sensors of both the electronic device and the external wearable device.

11. The method of claim 9, further comprising:

receiving, by the electronic device, at least one of an event associated with ending a function executed in the external device, an event associated with a communication disconnection with the external device, or an event associated with a change of the remaining capacity of a battery of the external device or the electronic device; and at least one of deactivating the activated sensor based on reception of the event or restoring a state of the sensor to a state before the external device connects with the electronic device in response to occurrence of the event.

12. The method of claim 9, wherein the sensor is an illumination sensor, and further comprising generating the menu based at least in part on illumination information indicating a dark condition.

13. The method of claim 9, further comprising collecting context information including sensor information and at least one of weather information, location information, time information, season information, event information of an area, advertisement information, information associated with the remaining capacity of a battery of the external device, or information associated with a communication channel state with the external device based on a communication interface; and collecting at least one of official anniversary information, personal anniversary information, personal schedule information or information associated with the remaining capacity of a battery of the electronic device, each of which is stored in a storage module of the electronic device.

14. The method of claim 9, further comprising:
generating, by the electronic device, a state information table for at least one of a sensor of the electronic device, activated or deactivated by a request of the external device, or a sensor of the electronic device, activated or deactivated by a request of the electronic device; and
storing the state information table.

15. The method of claim 14, further comprising:
updating, by the electronic device, the state information table, in response to the activation or deactivation of the sensor being changed by a request of the external device or a communication disconnection with the external device.

16. A method in an electronic device, comprising:
establishing, by the electronic device, a communication channel with an external wearable device;
generating screen control information based on collected context information;
transmitting, by a communication interface, the generated screen control information to the external wearable device, such that the external wearable device displays a menu based on the transmitted screen control information, wherein the menu includes a plurality of icons selectable on the external wearable device and respectively corresponding to a plurality of user's activities;
receiving, by the communication interface from the external wearable device, selection information corresponding to a selected icon from among one or more icons included in the menu; and
controlling at least one sensor of a plurality of sensors to be activated based on the received selection information,
wherein the plurality of user's activities includes at least one of walking, running, cycling, and climbing.

* * * * *